US012062463B2

(12) United States Patent
Park, Jr. et al.

(10) Patent No.: US 12,062,463 B2
(45) Date of Patent: Aug. 13, 2024

(54) NEUTRON TARGET FOR BORON NEUTRON CAPTURE THERAPY

(71) Applicant: Neutron Therapeutics LLC, Danvers, MA (US)

(72) Inventors: William H. Park, Jr., Marblehead, MA (US); Steven P. Konish, Peabody, MA (US); Theodore H. Smick, Gloucester, MA (US); Takao Sakase, Rowley, MA (US)

(73) Assignee: Neutron Therapeutics LLC, Danvers, MA (US)

( * ) Notice: Subject to any disclaimer, the term of this patent is extended or adjusted under 35 U.S.C. 154(b) by 145 days.

(21) Appl. No.: 17/302,412

(22) Filed: May 3, 2021

(65) Prior Publication Data

US 2021/0272716 A1 Sep. 2, 2021

Related U.S. Application Data

(63) Continuation of application No. 15/147,565, filed on May 5, 2016, now Pat. No. 11,024,437.

(Continued)

(51) Int. Cl.
*H05H 6/00* (2006.01)
*G21G 1/10* (2006.01)
(Continued)

(52) U.S. Cl.
CPC ............... *G21G 4/02* (2013.01); *G21G 1/10* (2013.01); *G21K 5/08* (2013.01); *G21K 5/10* (2013.01);
(Continued)

(58) Field of Classification Search
CPC ...... G21G 1/10; G21G 4/02; A61N 2005/109; A61N 2005/1081; H05H 3/06; H05H 6/00; G21K 5/02; G21K 5/08; G21K 5/10
See application file for complete search history.

(56) References Cited

U.S. PATENT DOCUMENTS 4,090,086 A 5/1978 Cranberg
4,112,306 A 9/1978 Nunan
(Continued)

FOREIGN PATENT DOCUMENTS

CN 204667894 9/2015
CN 205462125 8/2016
(Continued)

OTHER PUBLICATIONS

Surrey, et al., "FAFNIR: strategy and risk reduction in accelerator driven neutron sources for fusion materials irradiation data", Fusion Engineering and Design, 2014, pp. 2108-2113.
(Continued)

*Primary Examiner* — Sharon M Davis
(74) *Attorney, Agent, or Firm* — DLA PIPER LLP (US)

(57) ABSTRACT

Apparatuses and methods for producing neutrons for applications such as boron neutron capture therapy (BNCT) are described. An apparatus can include a rotary fixture with a coolant inlet and a coolant outlet, and a plurality of neutron-producing segments. Each neutron-producing segment of the plurality of neutron-producing segments is removably coupled to the rotary fixture, and includes a substrate having a coolant channel circuit defined therein and a solid neutron source layer disposed thereon. The coolant channel circuits are in fluid communication with the coolant inlet and the coolant outlet.

10 Claims, 26 Drawing Sheets

Related U.S. Application Data

(60) Provisional application No. 62/157,652, filed on May 6, 2015.

(51) Int. Cl.
*G21G 4/02* (2006.01)
*G21K 5/08* (2006.01)
*G21K 5/10* (2006.01)
*H05H 3/06* (2006.01)
*A61N 5/10* (2006.01)

(52) U.S. Cl.
CPC ............... *H05H 3/06* (2013.01); *H05H 6/00* (2013.01); *A61N 5/10* (2013.01); *A61N 5/1077* (2013.01); *A61N 2005/1087* (2013.01); *A61N 2005/109* (2013.01)

(56) References Cited

U.S. PATENT DOCUMENTS

| | | | |
|---|---|---|---|
| 4,360,495 | A | 11/1982 | Bauer |
| 4,582,667 | A | 4/1986 | Bauer |
| 5,392,319 | A | 2/1995 | Eggers |
| 5,870,447 | A | 2/1999 | Powell et al. |
| 9,974,979 | B2 | 5/2018 | Liu et al. |
| 2003/0152186 | A1 | 8/2003 | Jurczyk et al. |
| 2010/0067638 | A1 | 3/2010 | Zhuikov et al. |
| 2010/0067640 | A1 | 3/2010 | Willis et al. |
| 2012/0330084 | A1 | 12/2012 | Pantell et al. |
| 2013/0064338 | A1 | 3/2013 | Matsumoto et al. |
| 2015/0216029 | A1 | 7/2015 | Tsuchida |
| 2016/0270202 | A1 | 9/2016 | Shioda et al. |
| 2017/0082382 | A1 | 3/2017 | Mastinu et al. |
| 2018/0001112 | A1 | 1/2018 | Liu et al. |
| 2018/0114605 | A1 | 4/2018 | Chang et al. |
| 2018/0155368 | A1 | 6/2018 | Li et al. |

FOREIGN PATENT DOCUMENTS

| | | |
|---|---|---|
| CN | 205722821 | 11/2016 |
| CN | 106621071 | 5/2017 |
| JP | S51-98500 | 8/1976 |
| JP | S55-81500 | 6/1980 |
| WO | 2016/060867 | 4/2016 |
| WO | 2017/054548 | 4/2017 |
| WO | 2017/054557 | 4/2017 |
| WO | 2017/063407 | 4/2017 |
| WO | 2017054556 | 4/2017 |
| WO | 2017/080344 | 5/2017 |
| WO | 2017/084459 | 5/2017 |
| WO | 2017/088606 | 6/2017 |
| WO | 2017/097035 | 6/2017 |
| WO | 2017/114316 | 7/2017 |
| WO | 2017/114317 | 7/2017 |
| WO | 2017/162093 | 7/2017 |
| WO | 2017118291 | 7/2017 |
| WO | 2017121337 | 7/2017 |
| WO | 2017/088606 | 9/2017 |
| WO | 2017/181791 | 10/2017 |
| WO | 2017/206485 | 12/2017 |
| WO | 2018/006551 | 1/2018 |
| WO | 2018/076787 | 5/2018 |
| WO | 2018/076790 | 5/2018 |
| WO | 2018/086367 | 5/2018 |

OTHER PUBLICATIONS

Terrón, et al., "Union of Compact Accelerator-Driven Neutron Sources (UCANS) I & II Neutron applications laboratory for ESS-Bilbao", Physics Procedia 26, 2012, pp. 196-204.
Terrón, et al., "Conceptual design of the beryllium rotating target for the ESS-Bilbao facility", Nuclear Instruments and Methods in Physics Research Section A: Accelerators, Spectrometers, Detectors and Associated Equipment 724, 2013, 34-40.
Sordo, et al., "Baseline design of a low energy neutron source at ESS-Bilbao", Physics Procedia 60, 2014, pp. 125-137.
Bayanov, et al., "Neutron producing target for accelerator based neutron capture therapy", Journal of Physics: Conference Series, vol. 41. No. 1, IOP Publishing, 2006, pp. 460-465.
An English machine translation of Masaharu, et al., JP2007-303983, Nov. 22, 2007.
Blackburn, "High-power target development for accelerator-based neutron capture therapy", Department of Nuclear Engineering at the Massachusetts Institute of Technology, 2002, 229 pages.
Brown, et al., "Development of a high-power neutron-producing lithium target for boron neutron capture therapy." Penetrating Radiation Systems and Applications II. vol. 4142, International Society for Optics and Photonics, 2000, pp. 81-91.
International Search Report and Written Opinion issued on Aug. 5, 2016, in the international application No. PCT/US2016/030963, filed May 5, 2016, 12 pages.
Lee, et al., "Comparative analysis of jet impingement and microchannel cooling for high heat flux applications", International Journal of Heat and Mass Transfer 42.9, 1999, pp. 1555-1568.
Ludewigt, et al., "An epithermal neutron source for BNCT based on an ESQ-accelerator", Ernest Orlando Lawrence Berkeley National Laboratory, No. LBNL-40642; CONF-971125, Lawrence Berkeley National Lab, 1997, 14 pages.
Mastinu, et al., "The High Power Target for LENOS Project at Laboratori Nazionali di Legnaro of INFN-LNL", Workshop on Accelerator based Neutron Production ABNP, Apr. 2014, 29 pages.
Phoenix, et al., "The development of a BNCT facility at Birmingham University using a solid lithium target", Workshop on Accelerator based Neutron Production ABNP, Apr. 2014, 20 pages.
Powell, et al., "A New Target Concept for Proton Accelerator Driven Boron Neutron Capture Therapy Applications", Brookhaven National Laboratory, BNL-65825, Nov. 1998, 6 pages.
Taskaev, et al., "Development of lithium target for accelerator based neutron capture therapy", Target 1.1.6, 2006, 5 pages.

NEUTRON TARGET FOR BORON NEUTRON CAPTURE THERAPY

CROSS-REFERENCE TO RELATED APPLICATION

This application is a continuation of U.S. application Ser. No. 15/147,565, filed May 5, 2016, which claims priority to U.S. Provisional Application No. 62/157,652, filed May 6, 2015, the contents of which are hereby incorporated by reference herein in their entirety.

FIELD OF THE DISCLOSURE

The present disclosure relates to the methods and systems for generating neutrons using a neutron source material.

BACKGROUND

Neutron sources have many potential applications, including medical treatments, isotope production, explosive/fissile materials detection, assaying of precious metal ores, imaging, and others. A particular area of interest is boron neutron capture therapy (BNCT), which is a cancer treatment technique in which boron is preferentially concentrated in a patient's malignant tumor and a neutron beam is aimed through the patient at the boron-containing tumor. When the boron atoms capture a neutron, particles are produced having sufficient energy to cause severe damage to the tissue in which it is present. The effect is highly localized, and, as a result, this technique can be used as a highly selective cancer treatment method, effecting only specifically targeted cells.

Many activities employing neutron sources are presently carried out at nuclear research reactors where neutrons are plentiful. However, many practical issues such as safety, nuclear materials handling, and the approach of end-of life and decommissioning of many research reactors make this approach challenging. Accelerator-based neutron sources can be used as a relatively low-cost, compact alternative. For example, a small, relatively inexpensive linear accelerator can be used to accelerate ions, such as protons, which can then be focused on a target capable of generating neutrons. A primary challenge of this technology, however, is that traditional target architectures cannot adequately handle the high power that is imparted to the target by the proton beam, resulting in substantial damage to the target.

SUMMARY

Apparatuses and methods for producing neutrons for applications such as boron neutron capture therapy (BNCT) are described. An apparatus can include a rotary fixture with a coolant inlet and a coolant outlet, and a plurality of neutron-producing segments. Each neutron-producing segment of the plurality of neutron-producing segments is removably coupled to the rotary fixture, and includes a substrate having a coolant channel circuit defined therein and a solid neutron source layer disposed thereon. The coolant channel circuits are in fluid communication with the coolant inlet and the coolant outlet.

In some embodiments, an apparatus can include a rotary fixture with a coolant inlet and a coolant outlet, and a plurality of neutron-producing segments. Each neutron-producing segment of the plurality of neutron-producing segments is removably coupled to the rotary fixture. Each neutron-producing segment of the plurality of neutron-producing segments can include: a substrate having a coolant channel circuit defined therein, the coolant channel circuit in fluid communication with the coolant inlet and the coolant outlet; and a solid neutron source layer, for example comprising lithium, beryllium, or other neutron-generating material, disposed on a surface of the substrate. Each solid neutron source layer has a major surface that can be disposed substantially normal to an axis of rotation of the rotary fixture, disposed at a fixed angle (e.g., about 90 degrees, or about 0 degrees), or disposed substantially parallel with respect to an axis of rotation of the rotary fixture. The substrate can comprise at least one of copper, aluminum, titanium, and stainless steel. In some embodiments, the rotary fixture includes a vacuum seal.

In some embodiments, the coolant channel circuit includes a micro-channel with a dimension (e.g., a width or diameter), for example, of between about 0.5 mm and about 3 mm. The micro-channel can have a substantially circular or rectangular cross-sectional shape.

In some embodiments, the coolant channel circuit includes a plurality of substantially linear channels that are oriented substantially parallel to a major surface of the solid neutron source layer. Channels of the plurality of channels can be defined by a plurality of walls, each wall of the plurality of walls being disposed between two adjacent channels of the plurality of channels, each wall of the plurality of walls having a width that is about twice a width of each channel of the plurality of channels.

In some embodiments, each segment of the plurality of neutron-producing segments has a shape that is one of: a portion of an annulus, a sector, or a truncated sector. A thickness of the solid neutron source layer can be between about 0.01 mm and about 3 mm, or between about 0.09 mm and about 2 mm. The plurality of neutron-producing segments and the rotary fixture, collectively, can define a disk or drum having an outer diameter of about 1 meter. The plurality of neutron-producing segments includes at least 3, or at least 5, or a total of 16 neutron-producing segments.

In some embodiments, a method includes rotating a plurality of segments removably coupled to a rotary fixture, segments of the plurality of segments including a solid neutron source layer. A coolant is flowed through coolant channel circuits of the plurality of segments, and a proton beam is directed at the solid neutron source material such that the proton beam contacts a surface of each of a sequence of segments of the plurality of segments sequentially as the disk rotates (e.g., with a beam spot size of about 10 cm), so as to cause the emission of neutrons from the disk. The proton beam can have an energy of between about 1.88 MeV and about 3 MeV and/or a current of between about 10 mA and about 100 mA. The plurality of segments can be rotated at a speed of at least about 100 RPM, for example about 1,000 RPM.

BRIEF DESCRIPTION OF THE DRAWINGS

Specific embodiments of the present disclosure are described below and shown in FIGS. 1-18. These embodiments are being presented by way of example only. Numerous modifications and other embodiments are within the scope of one of ordinary skill in the art and are contemplated as falling within the scope of the present disclosure. In addition, those skilled in the art should appreciate that the specific conditions and configurations are exemplary and that actual conditions and configurations will depend on the specific system. Those skilled in the art will also be able to recognize and identify equivalents to the specific elements shown, using no more than routine experimentation.

DESCRIPTION

Figure 1A:
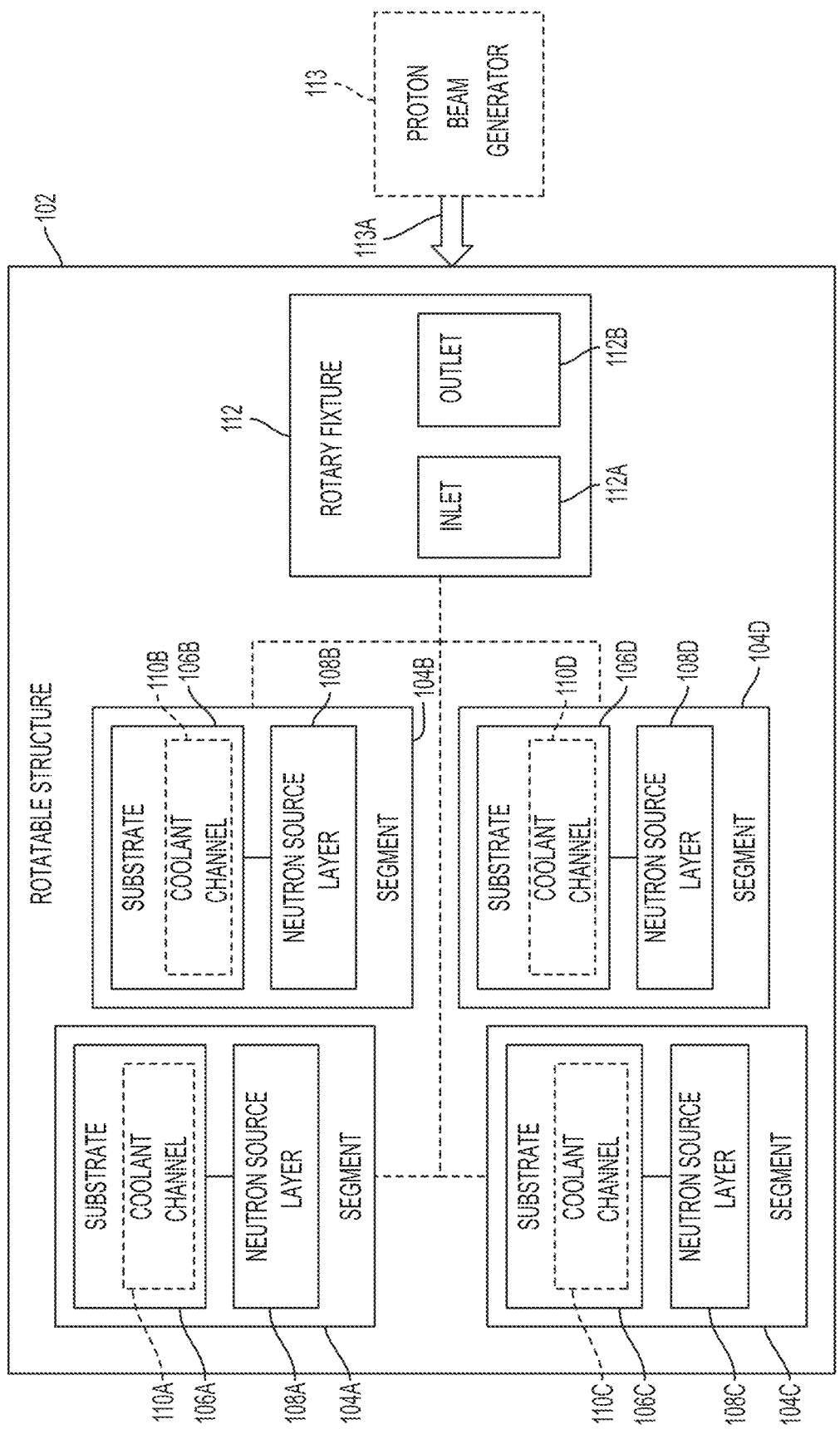
FIG. 1A is a block diagram of an apparatus suitable for use in boron neutron capture therapy (BNCT), in accordance with some embodiments of the present disclosure.

The present disclosure relates to methods, apparatuses and systems for generating neutrons. In some embodiments, a system includes a solid lithium neutron production target for boron neutron capture therapy (BNCT).

BNCT is a targeted radiation therapy for cancer treatment during which a patient is infused with a boron rich solution such as fructose-BPA. The boron is then selectively absorbed by the cancer cells, e.g., at a tumor site. Neutrons, for example, generated by a lithium neutron source, interact with the boron by the nuclear reaction: $^{10}B+n_{th}\rightarrow[^{11}B]^*\rightarrow\alpha+^7Li+2.31$ MeV. By irradiating the patient's tumor site with a flux of epithermal neutrons, which thermalize near the tumor site, the cancer cells are killed by the alpha particles and lithium ions. The alpha particles and lithium ions released have very short ranges, for example about 5-9 microns, and thus are similar in size to a cancer cell.

BNCT treatment requires a high flux of epithermal neutrons, typically between 1 eV and 10 keV. Fluxes required for clinical treatments are on the order of $1\times10^9$ n/cm$^2$/s. Historically, BNCT treatments have been performed at nuclear research reactor facilities, however accelerator-based neutron sources are preferred for widespread implementation of the treatment in hospital environments.

To produce the appropriate level of neutron flux using an accelerator, several nuclear reactions have been proposed. One of the most promising reactions is the $^7Li$ (p,n)$\rightarrow^7Be$ reaction. This reaction has a high neutron yield and produces neutrons of modest energy, both conditions being desirable for many applications. The neutron flux produced by this reaction is desirable for BNCT, for example because the flux can be easily moderated to epithermal neutrons without many high energy neutrons. To accomplish this reaction with an accelerator-based neutron source, a target bearing a source material (e.g., lithium) is presented to a proton beam generated by the proton accelerator. Neutrons are emitted from the source material and may be moderated and collimated by a beam shaping assembly into the desired neutron "beam" for treatment. The proton beam size can be of comparable size or smaller size than the neutron beam at the exit of the beam shaping assembly. For example, the proton beam size can be between about 40 mm and about 150 mm. There are two general approaches to the lithium P,N reaction for BNCT: "near threshold," where the proton beam energy is about 1.9 MeV, and "above threshold," where the proton beam energy is about 2.5 MeV. The "near threshold" approach has the advantage that the neutron energy distribution from the target is close to the epithermal energy distribution for treatment, thus only minimal moderation can be used. The "above threshold" approach produces a higher energy distribution of neutrons, and therefore can use more moderation, but takes advantage of a large peak in the reaction cross section at about 2.3 MeV resulting in a much higher initial yield of neutrons.

Lithium-based neutron generation for BNCT is typically performed according to one of two main approaches: using a film of liquid lithium flowing past the proton beam, and using lithium in solid form. Some liquid lithium approaches are based on work performed for the International Fusion Materials Irradiation Facility (IFMIF), and groups such as the Tokyo Institute of Technology in Japan, and Soreq NRC in Israel have built on this form specifically for BNCT.

There are at least three primary difficulties with accelerator-based neuron generation approaches. First, the material properties of solid lithium make it difficult to accommodate the high power (and associated heat) imparted to the target by the proton beam, since lithium has a relatively low melting temperature of 180°C and a modest thermal conductivity of 85 W/mK. If the energy of the proton beam, which is dissipated as heat in the target, is not efficiently removed, the target can be destroyed. Second, the $^7$Be produced from the P,N nuclear reaction is radioactive, releasing primarily a gamma at 0.5 MeV. Third, the hydrogen deposited in the target (e.g., in the lithium or in material below the lithium) may damage the target materials, limiting the lifetime of the target, and necessitating servicing of the target prior to failure.

Proposed approaches to heat removal have included: using a stationary solid target that is intensively cooled from its backside, and using a liquid target in which the beam impinges on a flowing jet of liquid source material. However, both of these approaches have significant drawbacks.

With regard to the stationary target approach, as noted above, lithium has a relatively low melting temperature and a relatively low thermal conductivity, which makes it challenging to safely remove or dissipate the high heat flux of the proton beam from the solid target without overheating and melting its surface. In addition, exposure to intense proton beams can quickly lead to blistering of the target materials and other hydrogen damage, such that frequent target replacement is needed, and the corresponding target lifetimes may not be practical for hospital applications such as BNCT. Cooling methods proposed for solid targets have included water jet impingement (e.g., groups at Massachusetts Institute of Technology and the University of Birmingham in the UK) and micro-channel cooling (e.g., Cancer Intelligence Care Systems at the National Cancer Center in Japan, and Ion Beam Applications in Belgium). Approaches proposed for extending the solid lithium target lifetime include: (1) using a thin layer of lithium (~50 to 100 microns, such that the protons are deposited behind the lithium) with a thin blister resistant material such as palladium or iron placed between the lithium and the copper; and (2) using thick lithium (>250 microns such that the protons are deposited in the lithium) and limiting the lifetime to whatever the lithium can handle before replacement.

An advantage of the liquid target approach is that the target can handle relatively high power densities and operate for very long periods without needing replacement. However, flowing liquid lithium approaches also require a large amount of lithium to fill up the circuit, pump and heat exchanger, which leads to both high cost and a significant safety hazard from the highly reactive lithium. Liquid lithium is corrosive, and when mixed with water can be explosive. In addition, a great deal of equipment is required to maintain the lithium in liquid form, pump it, exchange heat with it, and provide fire safety. Liquid lithium targets are considered by some to be unsuitable for a hospital setting. Liquid targets can suffer from slow heat-up times and potential solidification of flowing lithium if the temperature in the circuit drops too low, causing the charge of lithium to be inadvertently diverted into the target chamber.

Embodiments of the present disclosure overcome the neutron generation system issues described above using a direct-cooled, modularized rotating target architecture approach. For example, in some embodiments, a rotatable structure such as a disk or a drum includes a plurality of segmented target "petals" (also referred to herein as "segments") attached to a central hub (also referred to herein as a "rotary fixture"), where each petal is directly cooled via its own dedicated micro-channels. The plurality of target petals, collectively, may be said to constitute a target. Each petal can include a substrate and a solid neutron source layer disposed on a surface of the substrate. An exemplary system includes 16 petals on a planar rotatable structure, each petal occupying 22.5 degrees of a circumference of the rotatable structure, with the rotatable structure having an outer diameter (OD) of about 1 meter, and a semi-continuous strip of lithium deposited on the petals 0.14 meters in the radial direction centered on a 0.84 meter diameter.

Designs described herein offer several advantages over previous designs. First, previous micro-channel based techniques have typically been restricted to target dimensions of approximately 0.1 meter or less, for example because at larger target dimensions the pressure drop across the micro-channels is too large to be practical compared with other approaches. Using disk and drum designs set forth herein, a set of parallel fed micro-channel target segments each of approximately 0.1 meter in dimension are sequentially irradiated on a rotating structure, resulting in a micro-channel cooled area that is much larger than would be practical using a single inlet/outlet approach.

Second, the rotating structure configuration increases the cooled area between the neutron source (e.g., lithium) and the liquid coolant by at least an order of magnitude (limited, for example, by disk or drum diameter) over stationary targets without the need to angle the incident surface and suffer the inherent geometric inefficiencies in doing so.

Third, the segmentation of the target into a plurality of petals facilitates system servicing, in that the petals can be individually replaced, rather than the entire target. The rotational motion lends itself to a robotic petal exchange without the need to disturb the beam shaping assembly and embedded dosimetry equipment.

Fourth, the measurements can be compared with design data for the target, and the system can be shuttered or interlocked if the intensity exceeds a threshold or if the beam position is detected to be too far from the center (i.e., beyond a predetermined distance from the target center).

Segmented, Directly Cooled Rotating Targets for BNCT

FIG. 1A is a block diagram of an apparatus suitable for use in BNCT, in accordance with some embodiments of the present disclosure. As shown in FIG. 1, a rotatable structure 102 includes a plurality of target petals or segments 104A-104D, and each segment of the plurality of segments 104A-104D has a corresponding substrate 106A-106D coupled to a corresponding neutron source layer 108A-108D. The neutron source layer(s) 108A-108D can include solid lithium. One or more of the substrates 106A-106D includes a corresponding coolant channel (110A-110D), such as a micro-channel, for actively cooling the associated substrate and/or neutron source layer (e.g., to maintain the neutron source layer 108A-108D in solid form). The segments 104A-104D are optionally coupled to a rotary fixture 112 having an inlet 112A and an outlet 112B for conducting a coolant fluid. The segments 104A-104D can be coupled to the rotary fixture 112 via one or more of: screws, bolts, quick-disconnect fittings, clamps, and/or the like. The coolant fluid can include one or more of: water (e.g., deionized water, which provides higher heat capacity and thermal conductivity than oils, and lower corrosive activity as compared with city water), glycol, a glycol/water mixture, heat transfer oils (e.g., to avoid possible water/lithium interaction during a failure), "Galinstan" (a commercial liquid gallium/indium/ tin mixture), liquid nitrogen, and/or other coolants. The rotary fixture 112 can be configured to couple to an external spindle assembly and/or drive motor via a coupling such as a rotary water seal and/or a rotary vacuum seal. When the segments 104A-104D are connected to the rotary fixture 112, the coolant channels 110A-110D may be in sealed fluid communication with the inlet 112A and outlet 112B of the rotary fixture 112. FIG. 1A also depicts a proton beam generator 113 and a proton beam 113A.

Each segment of the segments 104A-104D can have a shape that is one of: a portion of an annulus, a pie-shape or "sector" (defined as the plane figure enclosed by two radii of a circle or ellipse and the arc between them), a truncated sector (i.e., a portion of a sector), a square, and a rectangle.

The neutron source layer 108A-108D can include lithium, beryllium, or another suitable neutron source in solid form and at a thickness that is sufficient to produce the desired neutron flux, for example for lithium at least about 10 μm, or at least about 90 μm (e.g., about 400 μm), or between about 10 μm and about 200 μm, or between about 90 μm and about 150 μm.

The neutron source layer 108A-108D can be adhered to the substrates 106A-106D of the segments 104A-104D via a thermal bond. For example, in some embodiments, one or more of the substrates 106A-106D include copper, and a "thick" lithium metal neutron source layer 108A-108D (e.g., having a thickness of 400 microns, where "thick" means greater than the proton range in lithium, which is about 300 microns) is bonded to the one or more copper substrates 106A-106D via a pressure and temperature method. As lithium is a reactive metal, it can form an amalgam with the copper. When properly bonded, a low thermal resistance between the copper and the lithium is formed. At such thicknesses of the neutron source layer(s) 108A-108D, the protons are deposited in the lithium during use, as opposed to the copper that underlies the lithium. In some cases, there is no drop in neutron yield up to doses of $1\times10^{19}$ ions/cm$^2$, and it can be expected that doses of $1\times10^{20}$ ions/cm$^2$ and beyond are possible. Unlike materials such as copper and aluminum, which exhibit an onset of blistering at doses near $\sim1\times10^{18}$ ions/cm$^2$, the lithium is softer, and without wishing to be bound by theory, it is considered that the hydrogen microbubbles that lead to blistering may not be able to form in the usual way in lithium, and as such, the hydrogen escapes without blister formation. The neutron source layer 108A-108D can change during irradiation, for example becoming more brittle and/or different in color, however as long as it remains intact and produces the same or nearly the same neutron yield, it is suitable for use.

Alternatively or in addition, the neutron source layer 108A-108D can be evaporated onto the substrates 106A-106D in a thin layer, for example of about 100 microns. A very thin, blister-resistant middle layer can be included in such designs as well (as has done in the stationary targets, described above). The base petal or substrate can be made of copper or aluminum. Even materials such as stainless steel, titanium, and molybdenum are possible since the distributed heat power is so much lower than in the stationary case.

The neutron source layers 108A-108D can be thermally bonded to the corresponding substrate 106A-106D, for example via a method developed at the University of Birmingham in the UK as described in A. V. Brown (2000) Development of a High-Power Neutron Producing Lithium Target for Boron Neutron Capture Therapy (Doctoral thesis). The system 100 can be configured for rapid, robotic target/petal exchange, can have a large thermal safety margin, and can be included in a Gantry design or other design for moving the radiation source rotationally about the patient isocenter.

In some embodiments, manufacturing of the coolant channels 110A-110D includes machining grooves into a surface of one or two halves of the corresponding substrate 106A-106D, for example using a milling or slot cutting tool. The two sides can then be bonded together such that the grooves define the coolant channels. The bonding can include brazing, soldering, and/or gluing. For brazing, copper can present a challenge because the brazing process brings the copper back to a dead soft condition even if it had been in a hard or half-hard state. Work hardening can be performed to temper the copper, for example using a set of rolling dies to bend the brazed copper assembly back and forth to achieve the temper. Other materials, such as aluminum, can be tempered using heat and quench methods that do not involve deformation of the part. When brazing or soldering, the coolant channels 110A-110D may be inspected to ensure that the braze or solder material has not wicked into the channels, which could reduce their flow or even block them completely. Alternatively, the coolant channels 110A-110D can be machined as through-holes, for example via milling, electrical discharge milling, "hole popping," or drilling (e.g., chemical drilling, gun drilling, etc.). Through holes can be easily inspected for blockage, and it does not remove the temper of the material. Caps on each end of the coolant channels 110A-110D can then be welded (e.g., electron beam welded) to each end to provide the feed, return, and turnaround fluid passages. Alternatively or in addition to electron beam welding, the caps can be secured to the coolant channels 110A-110D via tungsten inert gas (TIG) welding, soldering, friction welding, an o-ring, or other methods. Alternatively or in addition, the coolant channels 110A-110D can be formed by brazing tubes (e.g., thin walled copper tubes) to a plate.

A variety of different coolant channel geometries and fabrication approaches are contemplated by the present disclosure. For example, a cross-sectional shape of the coolant channels 110A-110D can be round or rectangular, with dimensions ranging from about 0.5 mm to about 1.5 mm (i.e., micro-channels), or up to 3 mm.

In some embodiments, the cooling channels 110A-110D are defined by a plurality of walls, each wall of the plurality of walls being disposed between two adjacent cooling channels 110A-110D. Each wall of the plurality of walls has a width that can be a factor wider than an adjacent channel. For example, each wall can be about twice a width of an adjacent cooling channel of the cooling channels 110A-110D.

The lengths of the coolant channels 110A-110D can be substantially equal to one another and on the order of, or larger than, the beam size, for example about 140 mm long for a 120 mm diameter beam. The size (e.g., lengths) of the channels can be selected/designed based on the beam size. The channel-to-channel pitch can also be designed according to the desired application. For example, in some embodiments, a "2:1 pitch" is used, which can refer to a 1 mm channel that is followed by a 1 mm wall, followed by another 1 mm channel etc. In some embodiments, the petal channels have a 3:1 pitch, for example 1 mm channels with 2 mm walls separating them. A 3:1 pitch can reduce the total flow of coolant while adequately cooling the petal, while a 2:1 pitch can be more effective at cooling (but at a higher total coolant flow).

Figure 1C:
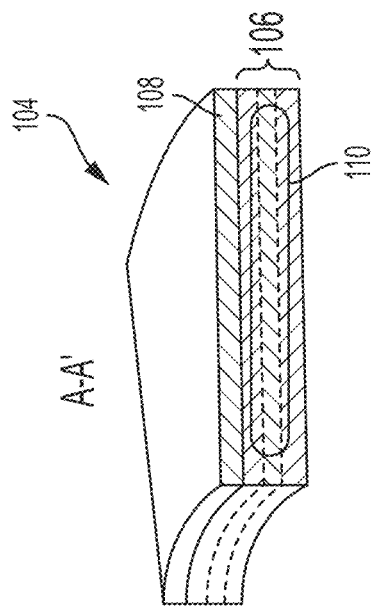
FIG. 1C is a diagram showing a cross-sectional view of the rotatable structure of FIG. 1B, corresponding to line A-A' of FIG. 1B.
Figure 1B:
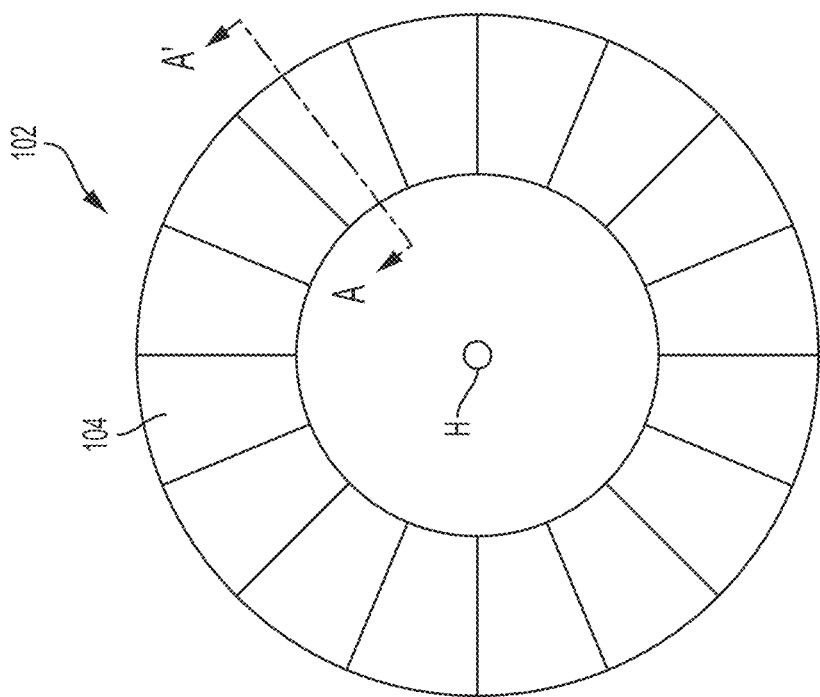
FIG. 1B is a diagram of a plan view of a disk-shaped rotatable structure, in accordance with some embodiments.

FIG. 1B is a diagram of a plan view of a disk-shaped rotatable structure, in accordance with some embodiments. As shown, the rotatable structure 102 has a central hub portion "H" with a plurality of segments 104 attached thereto and emanating therefrom. The segments 104 each include a corresponding neutron source layer with a major surface that can be, for example, substantially normal to an axis of rotation of the rotatable structure 102. The axis of rotation may be defined as an axis that passes through the center of the hub "H" and is substantially normal thereto. FIG. 1C is a diagram showing a cross-sectional view of the rotatable structure of FIG. 1B, corresponding to line A-A' of FIG. 1B. As shown in FIG. 1C, a neutron source layer 108 is disposed on a substrate 106 with an embedded coolant channel 110.

Figure 1D:
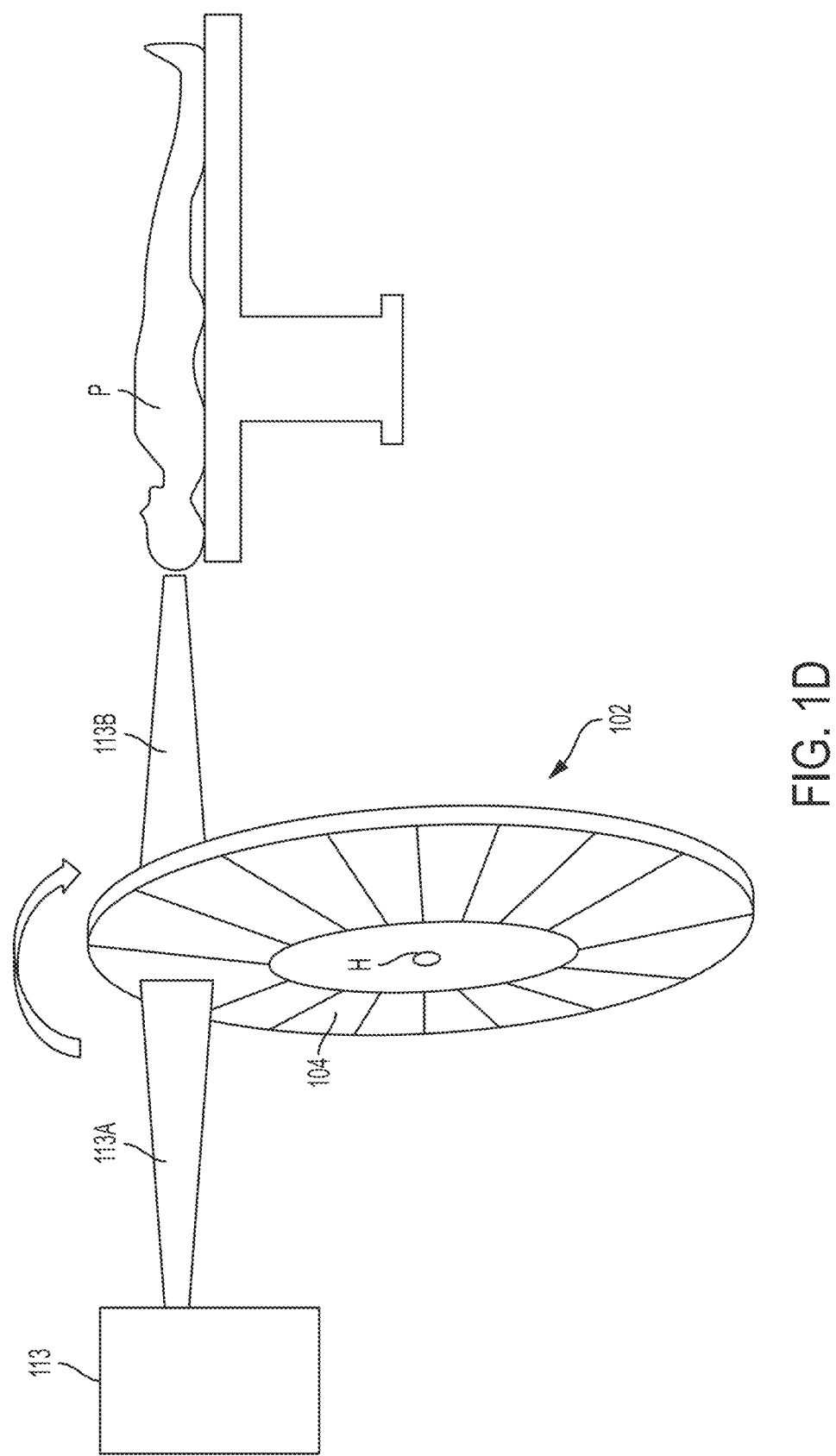
FIG. 1D is a diagram of the rotatable structure of FIG. 1B during use as part of boron neutron capture therapy (BNCT), in accordance with some embodiments.

FIG. 1D is a diagram of the rotatable structure of FIG. 1B during use as part of boron neutron capture therapy (BNCT), in accordance with some embodiments. As shown, the rotatable structure 102 is rotating about its axis of rotation, and a proton beam generator 113 emits a proton beam 113 toward the rotatable structure 102 such that the proton beam 113A contacts a surface of the rotatable structure 102, e.g., at a neutron source layer of a segment 104. The proton beam 113A can be stationary (e.g., at a predetermined position) or rastering over a predetermined region of the rotatable structure 102, where the predetermined region may be fixed or may change over time. The proton beam 113A can form an angle with the contacting surface of the rotatable structure 102, for example of about 90°. Since the rotatable structure 102 is rotating, segments 104 of the rotatable structure 102 can be sequentially contacted by the proton beam 113A. As a result of the interaction of the proton beam 113A with the neutron source layer of segment(s) 104, a neutron beam 113B is generated and directed (e.g., via a collimator or other beam-shaping structure) towards a treatment area of a patient P.

Figure 1F:
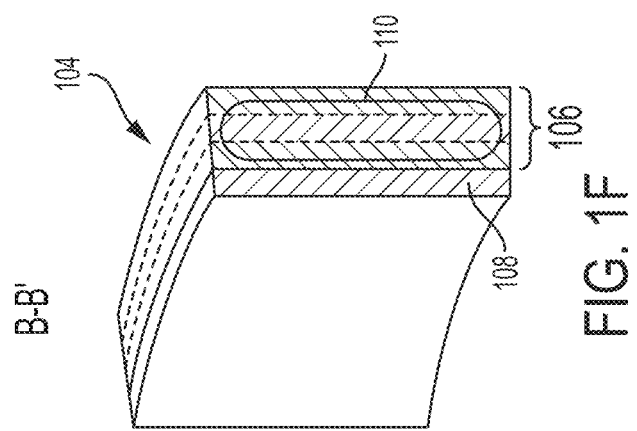
FIG. 1F is a diagram showing a cross-sectional view of the rotatable structure of FIG. 1E, corresponding to line B-B' of FIG. 1E.
Figure 1E:
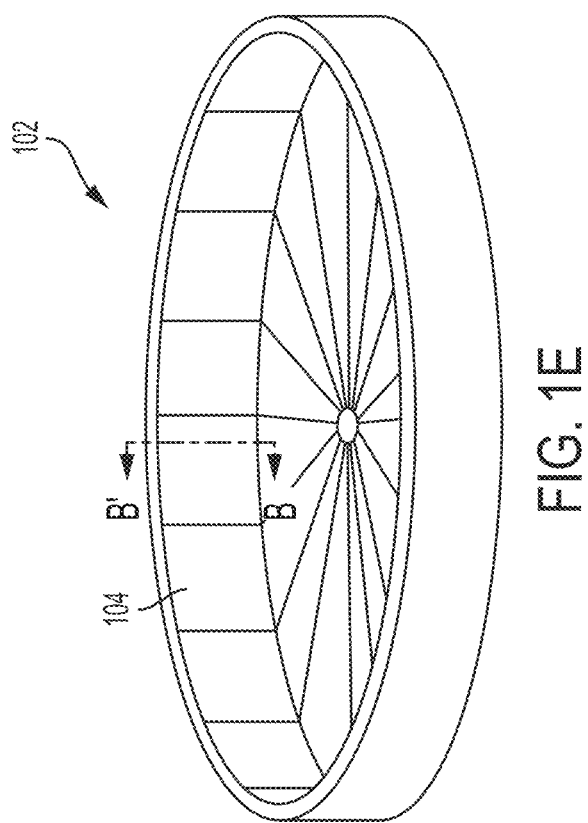
FIG. 1E is a diagram of a perspective view of a drum-shaped rotatable structure, in accordance with some embodiments.

FIG. 1E is a diagram of a perspective view of a drum-shaped rotatable structure, in accordance with some embodiments. As shown, the rotatable structure 102 has a base portion and a plurality of segments 104 attached thereto and emanating therefrom, the segments forming a fixed angle with respect to the base (e.g., 90°, or an angle of at least 45°). The segments 104 include a neutron source layer with a major surface that can be, for example, substantially parallel to an axis of rotation of the rotatable structure 102. The axis of rotation may be defined as an axis that passes through the center of the base portion and is substantially normal thereto. FIG. 1F is a diagram showing a cross-sectional view of a segment-bearing portion of the rotatable structure of FIG. 1E, corresponding to line B-B' of FIG. 1E. A neutron source layer 108 is disposed on a substrate 106 with an embedded coolant channel 110.

Figure 1G:
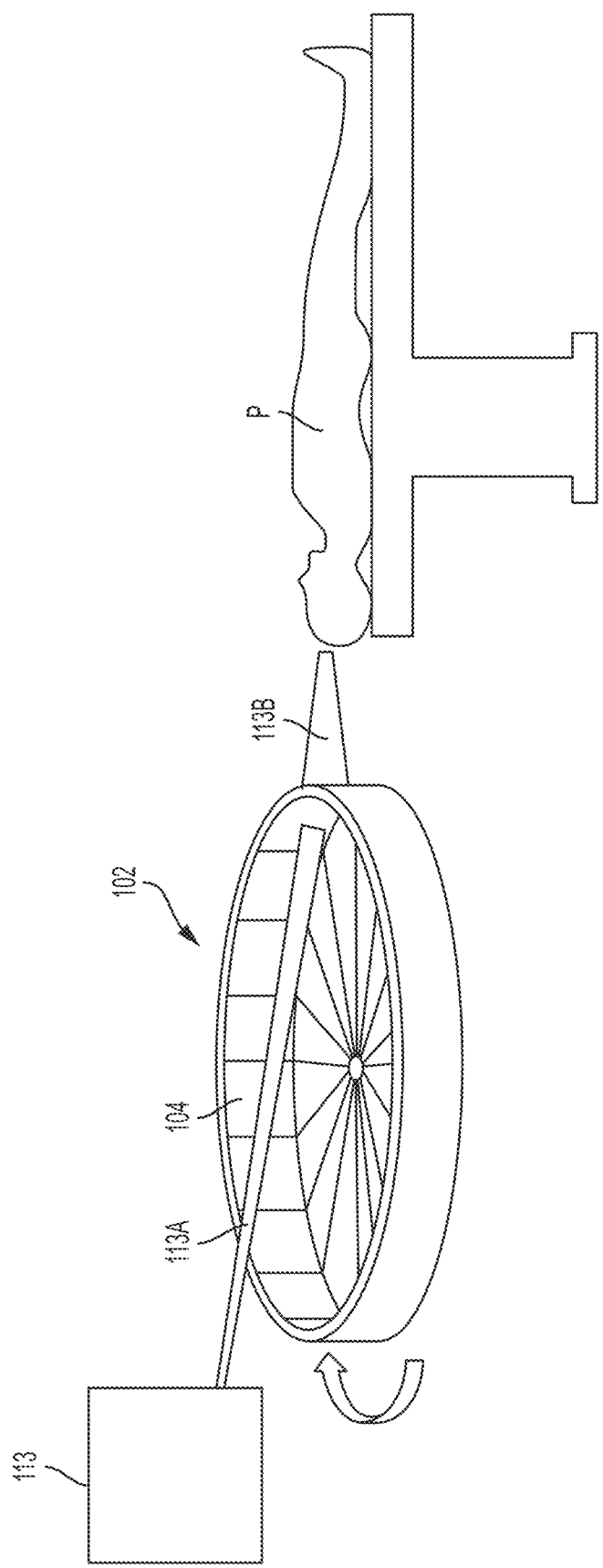
FIG. 1G is a diagram of the rotatable structure of FIG. 1E during use as part of BNCT, in accordance with some embodiments.

FIG. 1G is a diagram of the rotatable structure of FIG. 1E during use as part of BNCT, in accordance with some embodiments. As shown, the drum-shaped rotatable structure 102 is rotating about its axis of rotation, and a proton beam generator 113 emits a proton beam 113 toward the rotatable structure 102 such that the proton beam 113A contacts a surface of the rotatable structure 102, e.g., at a neutron source layer of a segment 104. The proton beam 113A can be stationary (e.g., at a predetermined position) or rastering over a predetermined region of the rotatable structure 102, where the predetermined region may be fixed or may change over time. The proton beam 113A can form an angle with the contacting surface of the rotatable structure 102, for example of about 90°. Since the rotatable structure 102 is rotating, segments 104 of the rotatable structure 102 can be sequentially contacted by the proton beam 113A. As a result of the interaction of the proton beam 113A with the neutron source layer of segment(s) 104, a neutron beam 113B is generated and directed (e.g., via a collimator or other beam-shaping structure) towards a treatment area of a patient P.

Figure 2:
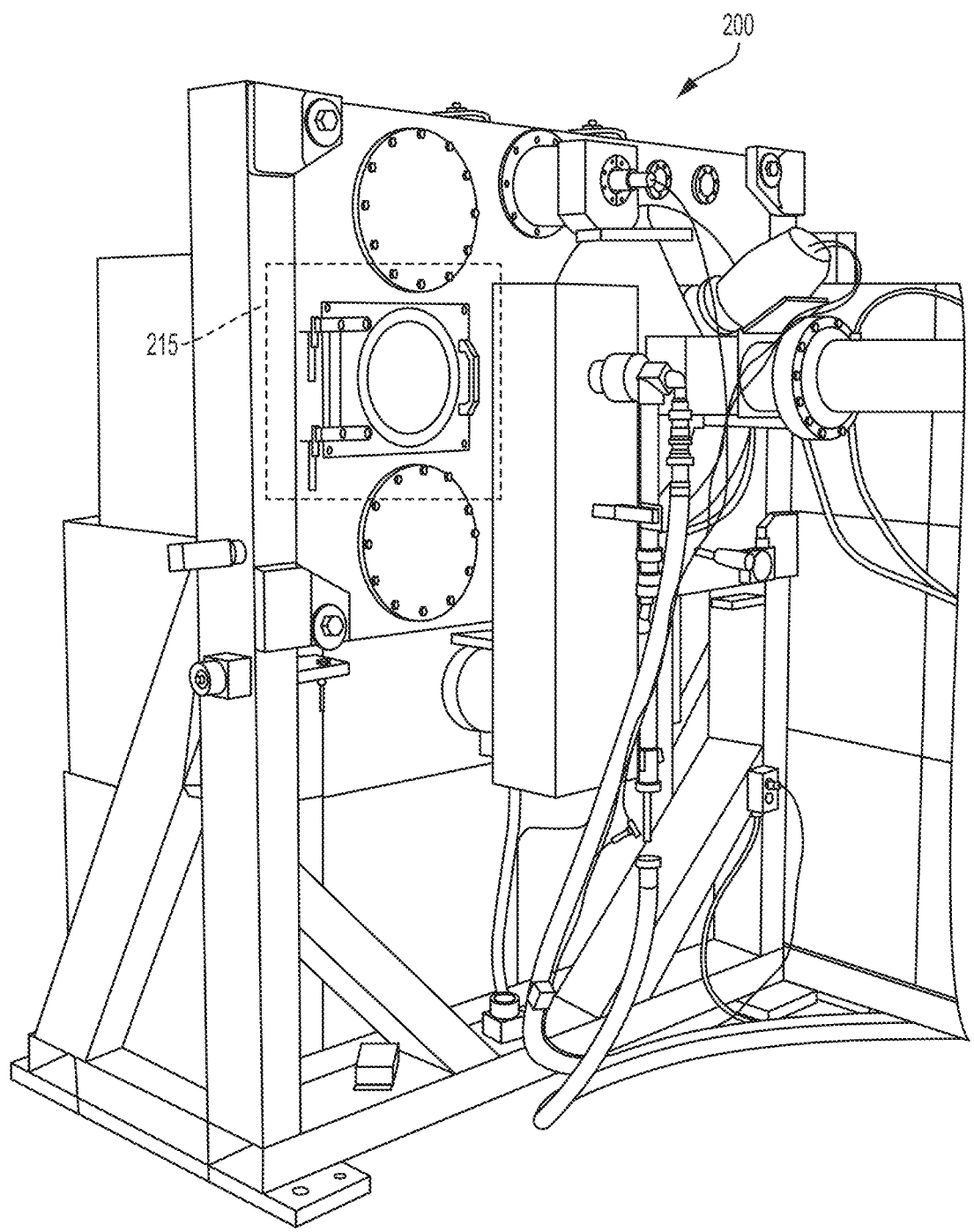
FIG. 2 is a depiction of a BNCT apparatus, in accordance with some embodiments of the present disclosure.
Figure 3:
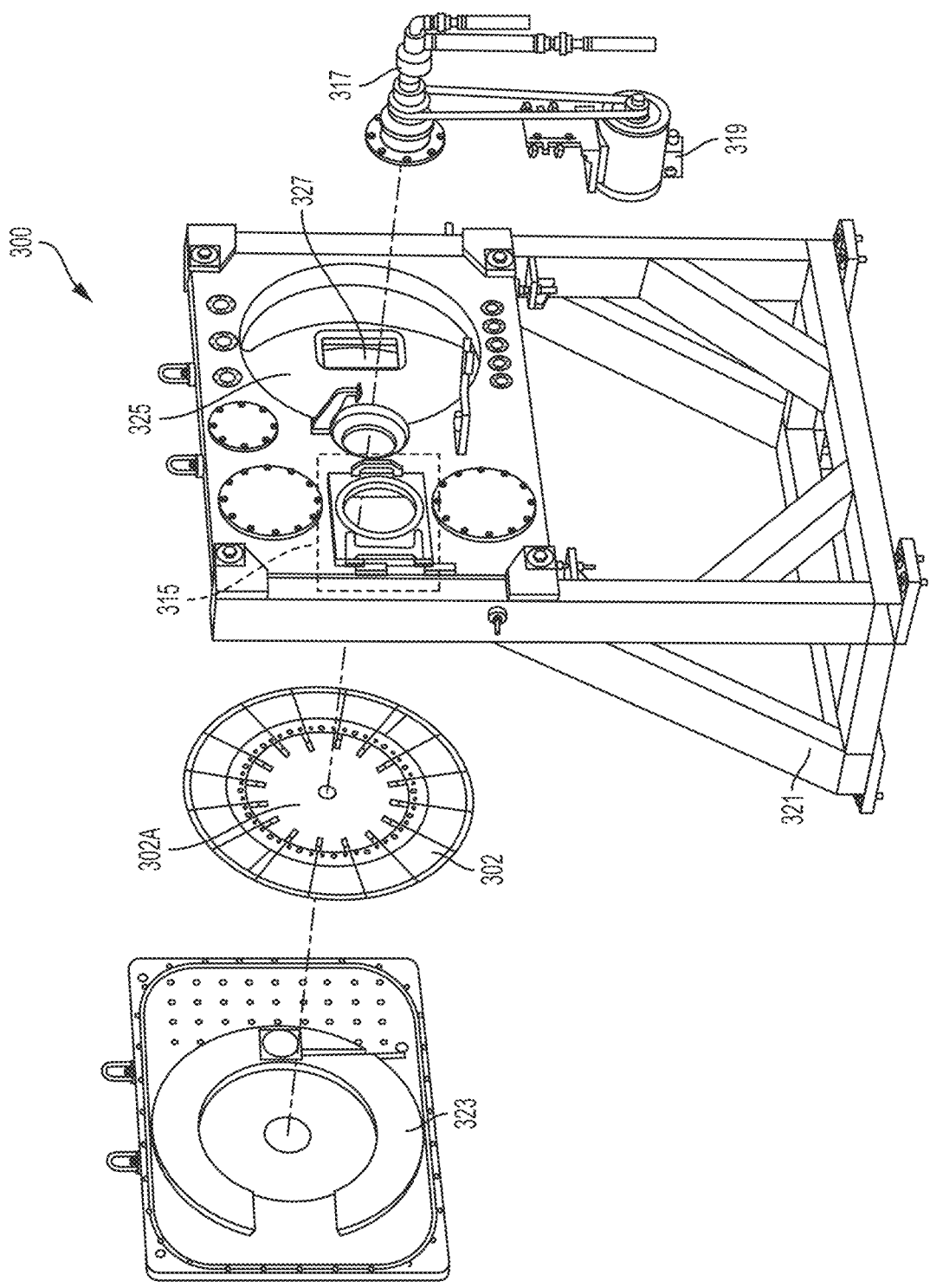
FIG. 3 is a rendering of an exploded view of a BNCT apparatus, in accordance with some embodiments of the present disclosure.

FIG. 2 is a depiction of a BNCT apparatus 200, in accordance with certain embodiments, showing a chamber access door 215. FIG. 3 is a rendering of an exploded view of a BNCT apparatus 300, similar to the BNCT apparatus 200 of FIG. 2, in accordance with certain embodiments. As shown in FIG. 3, apparatus 300 includes a frame 321, a chamber 325 with an aperture 327 defined therein, and a chamber access door 315. A target disk 302 with a hub 302A is dimensioned to fit within the chamber 325, and, when installed in the chamber, is secured to the chamber and frame 321 via the back cover 323. A spindle assembly 317 is configured to mechanically couple to the hub 302A of the target disk 302, and to rotate the target disk 302 when driven by a spin motor 319. Although shown and described in FIG. 3 to be a disk, other target geometries, such as barrels, drums, cylinders, etc., are also contemplated.

Figure 4B:
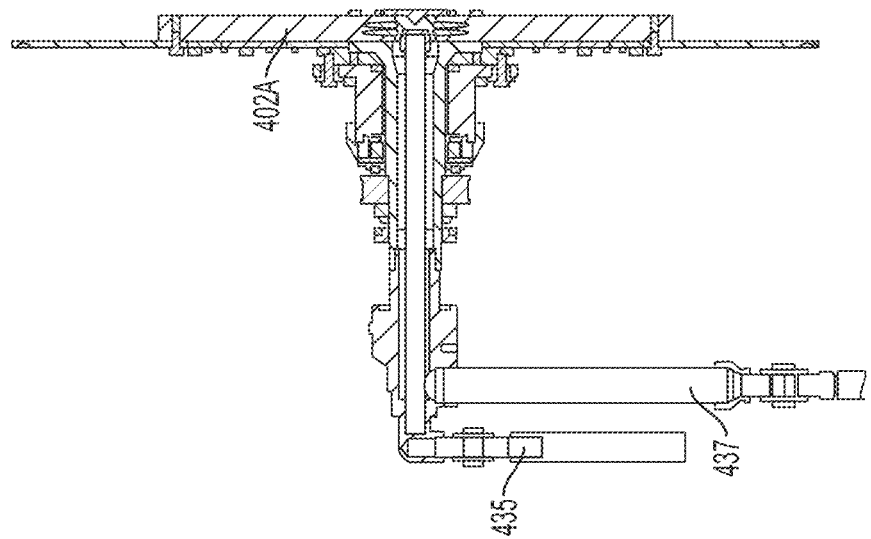
FIG. 4B is a rendering of a side view of the rotatable target assembly of FIG. 4A.
Figure 4A:
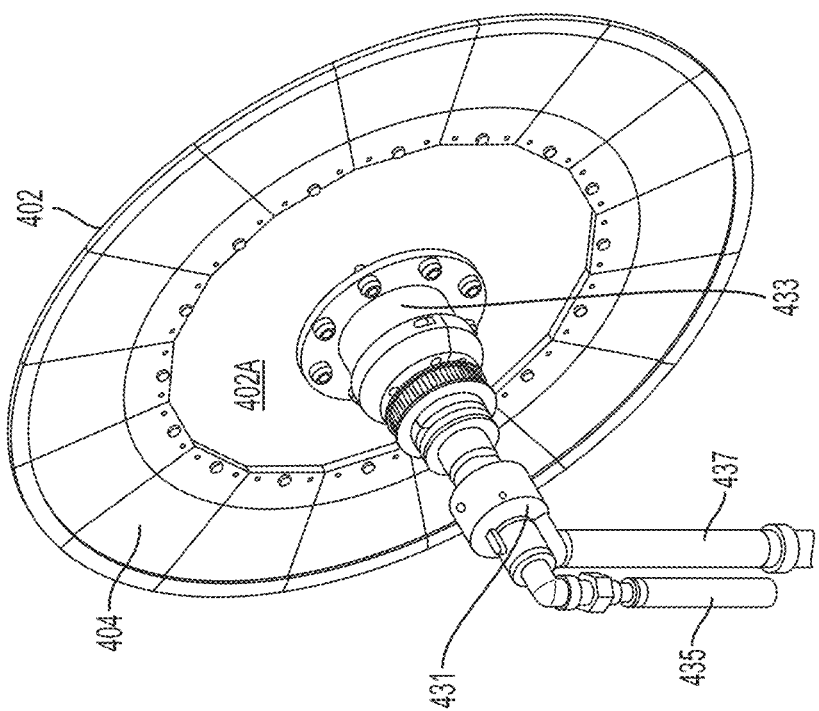
FIG. 4A is a rendering of a perspective view of a rotatable target assembly, in accordance with some embodiments of the present disclosure.

FIG. 4A is a rendering of a perspective view of a rotatable target assembly, in accordance with certain embodiments. Moving coolant into and out of the rotatable structure 102 is a special engineering challenge. In some embodiments of the present disclosure, a ferrofluidic rotary air-to-vacuum seal with coaxial fluid in out flow is used, followed by a dual flow rotary fluid to air seal such as a "Deublin" seal. As shown in FIG. 4A, the rotatable target assembly 402 includes a hub 402A and a plurality of removable target petals 404. A first end of a ferrofluidic rotary vacuum seal 433 is mounted to the hub 402A, and a second end of the ferrofluidic rotary vacuum seal 433 is coupled to a coolant inlet 435 and a coolant outlet 437 via a water seal (e.g., a Deublin rotary water seal) 431. FIG. 4B is a rendering of a side view of the rotatable target assembly of FIG. 4A.

Figure 5B:
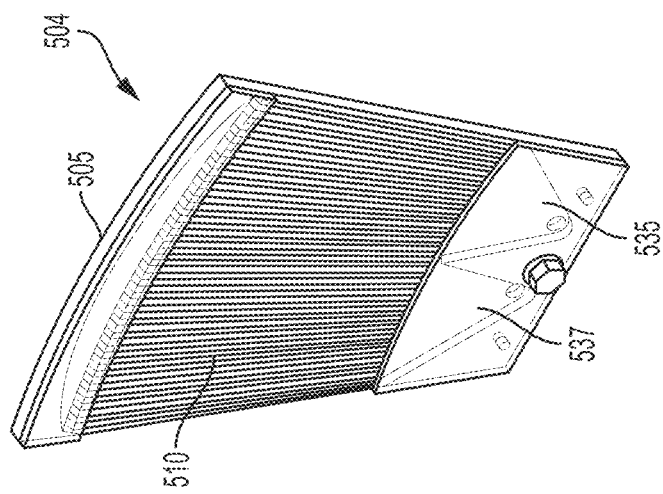
FIG. 5B is a rendering of a perspective view of a petal, showing micro-channels, in accordance with some embodiments of the present disclosure.
Figure 5A:
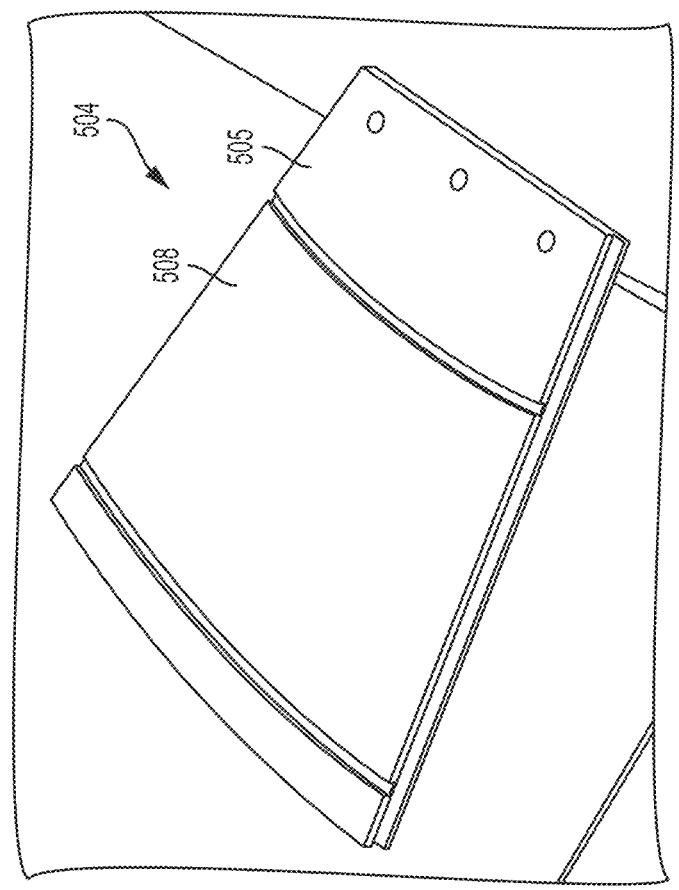
FIG. 5A is a depiction of a petal, in accordance with some embodiments of the present disclosure.

FIG. 5A is a depiction of a front view of a petal, such as a petal 404 of FIG. 4A, in accordance with some embodiments of the present disclosure. The petal 504 can include a substrate 505, which can include copper, aluminum, or other material (e.g., a ceramic material), and an optional metallized surface 508 (e.g., a copper, palladium film) onto which lithium is to be placed. The metallized surface 508 can be formed via plating (e.g., electrochemical plating), physical vapor deposition metal painting, etc. FIG. 5B is a rendering of a rear perspective view of a petal, showing microchannels, in accordance with certain embodiments. The petal 504 includes a water inlet 535, a water outlet 537, and a plurality of cooling micro-channels 510 having a cross-sectional area, by way of example, of about 1 mm×0.75 mm. Although shown and described with reference to FIG. 5B to include a "water inlet" and a "water outlet," alternatively or in addition any other type of cooling fluid may be used. Also, although shown and described with reference to FIG. 5B to have rectangular cross-sections, the micro-channels of petals described herein can have any other cross-sectional shape, such as circular, square, polygonal, etc.

Robotic Petal Exchange

Figure 6:
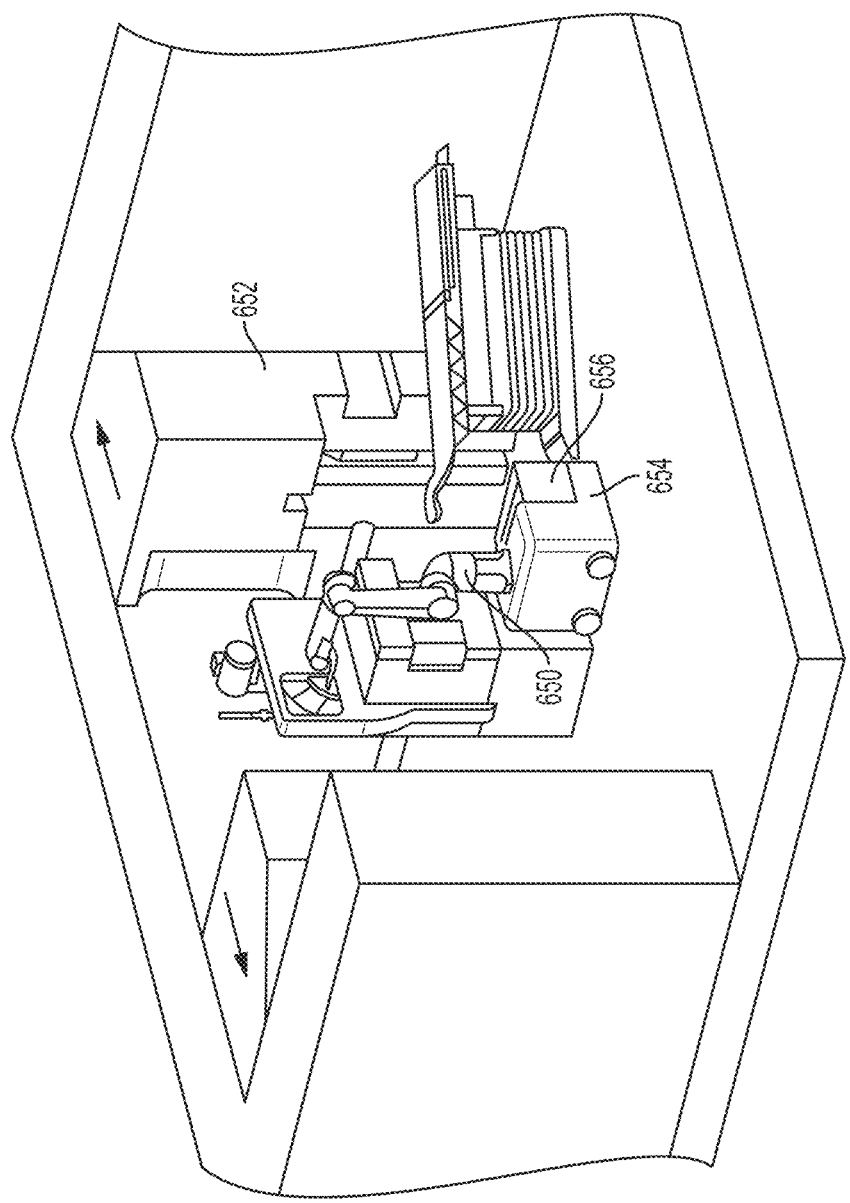
FIG. 6 is an illustration of a robotic exchange apparatus, in accordance with some embodiments of the present disclosure.

As noted above, a promising reaction for generating neutron flux using an accelerator is the $^7Li$ $(p,n) \rightarrow ^7Be$ reaction. However, since the lithium P,N reaction creates $^7Be$ which is radioactive, ~0.5 MeV photons are emitted and a high radiation field is present. As such, in some implementations, a BNCT system includes a robot to perform the exchange of spent/used petals/segments, so as to limit the radiation exposure to workers (to level that is as low as reasonably achievable, "ALARA"). FIG. 6 shows an example of a system configured for robotic target servicing (i.e., a robotic exchange apparatus). As shown in FIG. 6, a commercial off-the-shelf industrial robot 650, such as those manufactured by the US company FANUC and the Swiss company Stäubli, either already present in the room or brought into the room (e.g., via a mobile robot cart 654) for the purpose of servicing a target, is positioned in front of the target. During the robot-controlled target exchange, workers can leave the room and close the vault room shielding door. At this point, one or more retractable target shields 652 open, revealing a vacuum port via which the target petals can be accessed by the robot 650. The robot can remove the spent/used petals one by one, for example by indexing the rotatable structure, and place them in or transport them to a shielded box 656, such as a lead lined box (also referred to as a "pig"), to prevent radiation exposure to workers. Also, since the lithium is reactive with moist air, the stored petals can be kept in a non-reactive medium, such as argon or mineral oil, so as to prevent the $^7$Be from becoming airborne.

Replacement (e.g., fresh new or recycled) petals can either be installed at this point or installed later, either by the robot 650 or manually. Since lithium interacts with moist air, the environment of the room may be kept very dry, preferably at about 1% to 2% relative humidity during the exchange, and the room can be humidified once the vacuum is returned to the system. Alternatively, a glove box with load locks can be used, e.g., with a robot 650 inside the glove box, to remove and/or install the petals.

In some embodiments, the robot 650 remains in the treatment room on a track, and only the shielding box 656 is transported into and out of the room.

In some embodiments, the robot 650 is performs unloading of target petals, but not installation.

Petal Designs

Figure 7B:
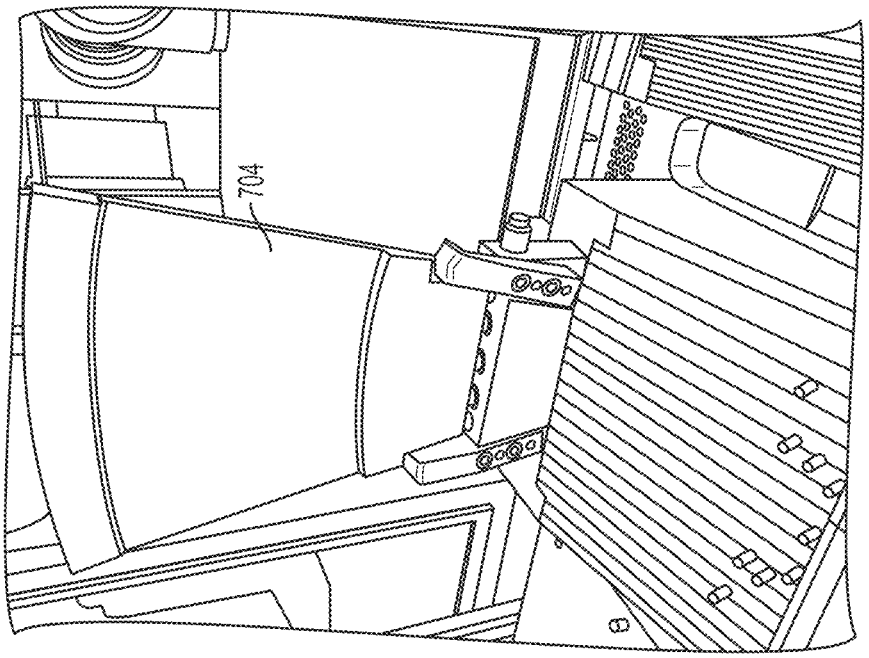
FIG. 7B is a depiction of the petal of FIG. 7A, attached to a hub, according to some aspects of the present disclosure.
Figure 7A:
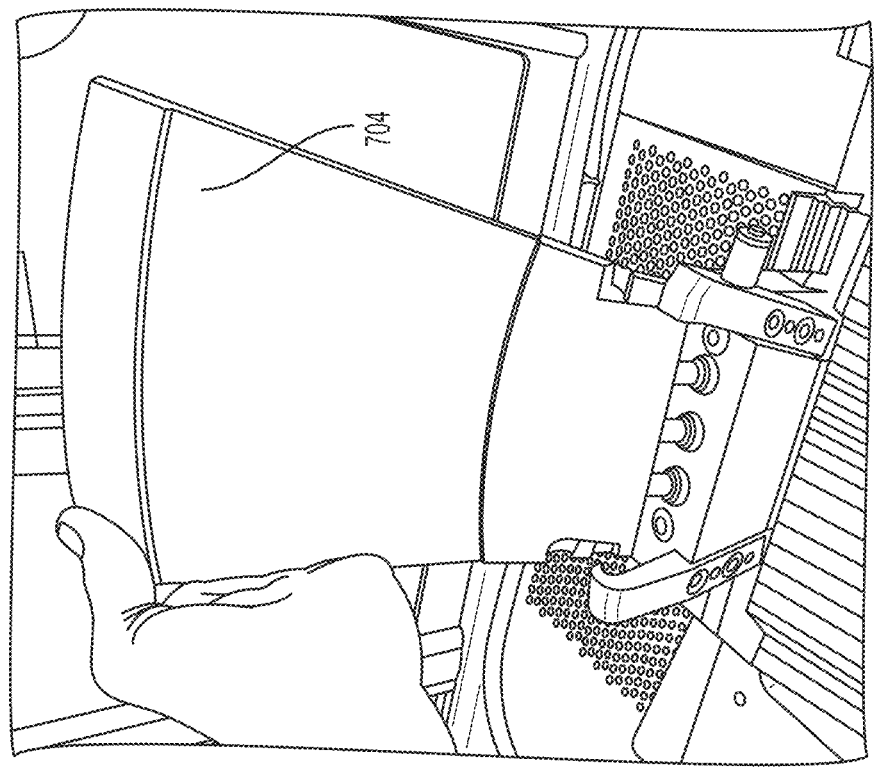
FIG. 7A is a depiction of petal attachment, in accordance with some embodiments of the present disclosure.

Petals can be attachable to a rotary fixture (or "hub") in a variety of ways. One method, shown in FIGS. 3-5, utilizes a face seal constrained by locating pins and held fixed by a bolt. In other embodiments, machined locating features can be incorporated into the parts, and instead of a bolt, an over center clamp can be used to constrain the part. The attachment mechanism should be selected to withstand significant centrifugal spin forces. In still other embodiments, a method for attaching petals to the hub is shown in FIGS. 7A-7B. In some embodiments, this method can use piston seals rather than face seals to seal the water from the hub to the petal 704. In addition, the seals can be machined to allow them to be inserted at an angle to slide under a set of fixed fences. Spring plungers can retain the petal in position once the robot has let go of the petal. Once spinning, the centrifugal forces lock the petal against the fences. There are several advantages to this design. First, there are no thread forms that can get stuck or galled and result in a failure of the process. Second, the piston seal is substantially aligned with the radial fluid feeds in the hub, thereby eliminating two 90° bends in the flow and reducing the pressure drop across the system. Third, the mechanism is low profile and elegant compared with other clamping mechanisms that may be considered.

In some embodiments, a micro-channel arrangement includes two sets of micro-channel arrays, as shown in FIGS. 8A-8D, for a petal 804 having micro-channels 810, water inlet 837 and water outlet 835. This design allows the micro-channels to get very close to the edge of the corresponding petal (i.e., nearer to the space between the petals). In other embodiments, a larger return path behind the micro channels is used in order to reduce the pressure drop across the petal, however this design also makes the overall petal thicker and uses a higher total flow for a given fluid velocity in the micro-channels.

Petal Performance

A simulation of petal cooling for the micro-channel arrangement with two sets of micro-channel arrays was performed. The simulation parameters were defined as follows:

Proton beam: 2.6 MeV, 30 mA (78 kW), Gaussian beam approximation, $\sigma=20$, $\pm3$ $\sigma=\phi120$ mm (99.7%)

Water flow: 0.002 m$^3$/s total (32 gal/min, 2 gal/min per petal), 20° C. inlet temperature Target disk: Centerline diameter: $\phi840$ mm, Rotational speed: 10 Hz (600 RPM)

Lithium thickness: 400 µm.

Figure 8A:
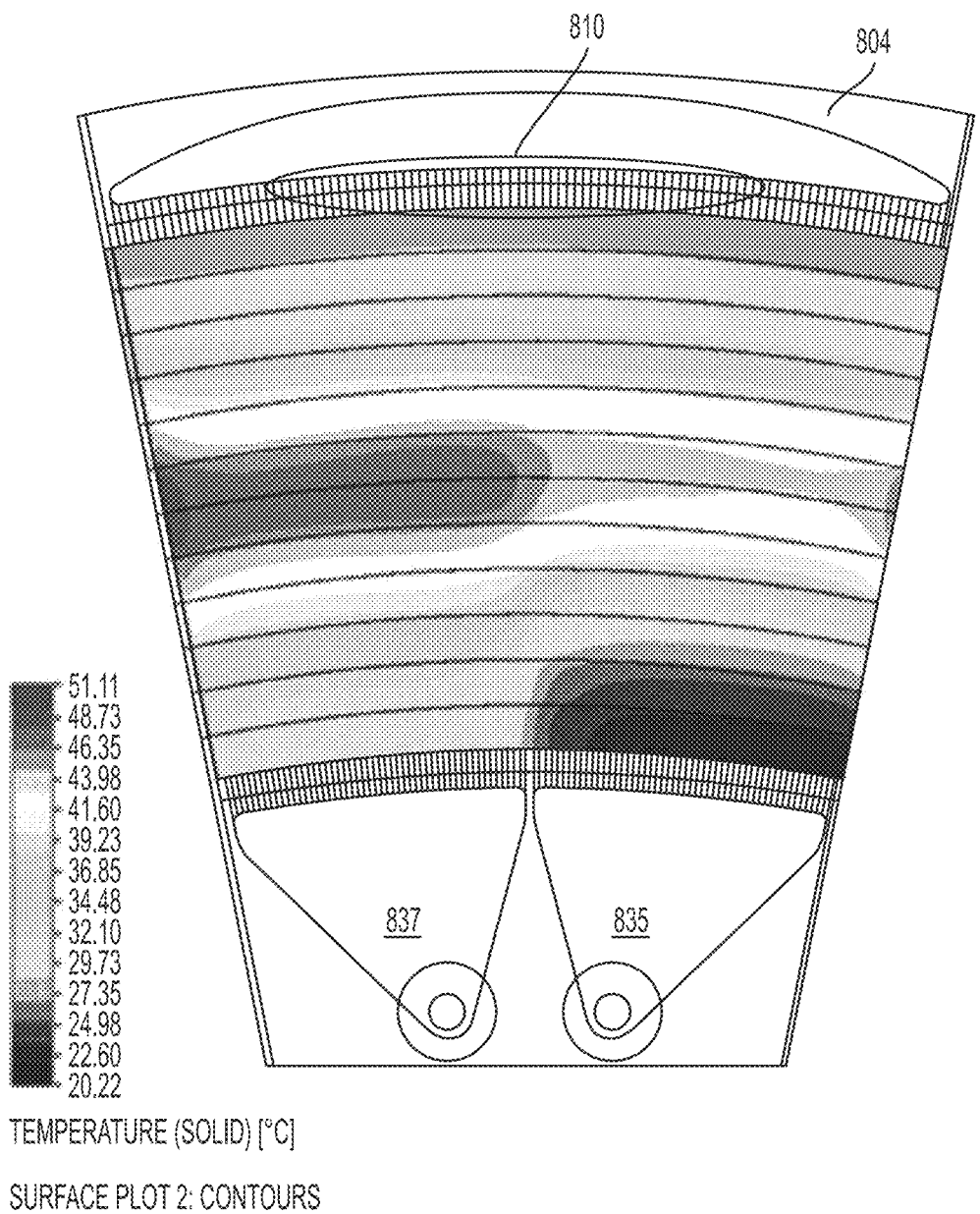
FIG. 8A is a thermal map, showing average lithium surface temperature for a micro-channel arrangement, in accordance with some embodiments of the present disclosure.
Figure 8B:
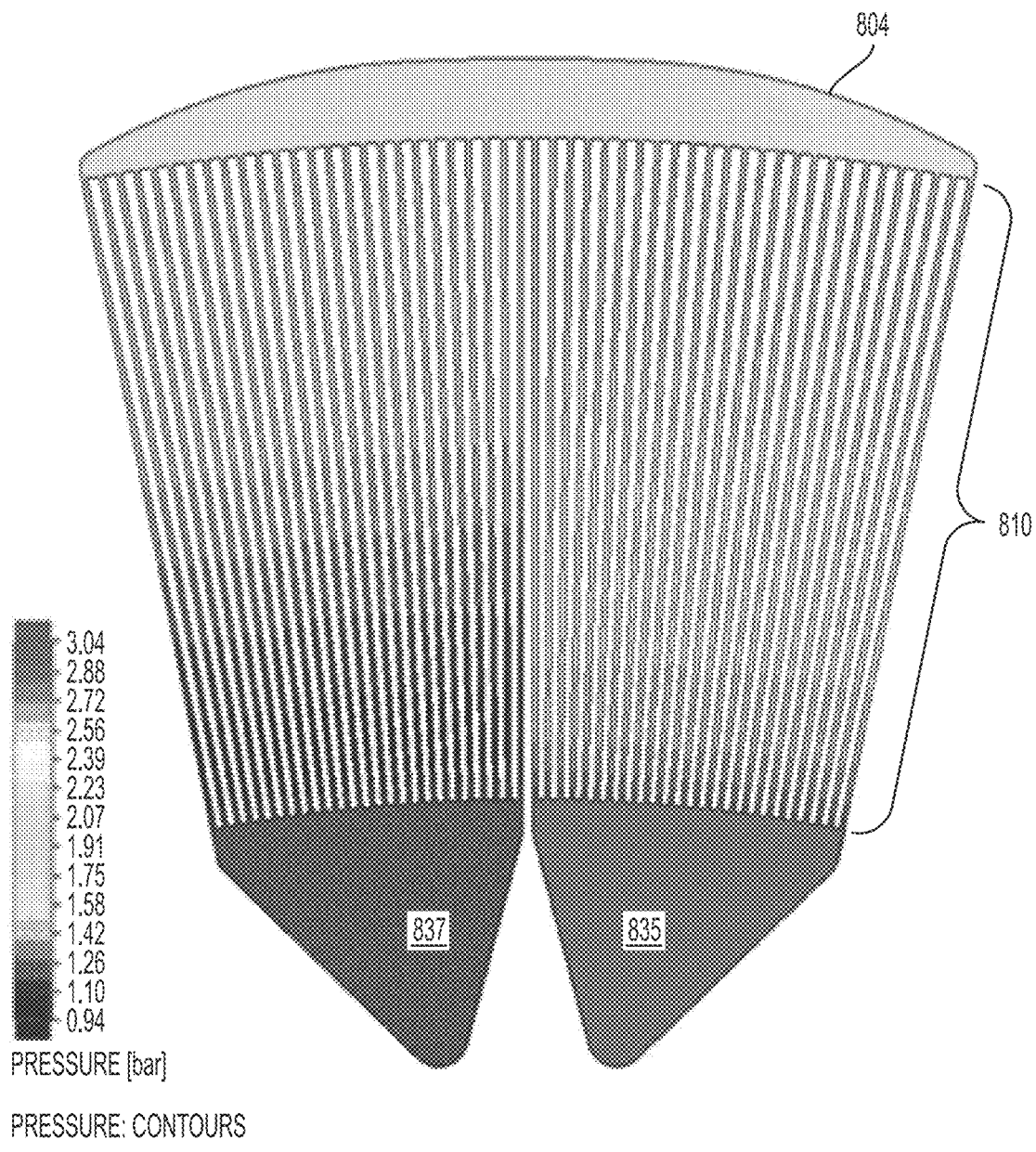
FIG. 8B is a pressure map of the micro-channel arrangement of FIG. 8A.

FIGS. 8A-8D show the results of the simulation. For example, FIG. 8A is a thermal map of a petal 804, showing the distribution of the average lithium surface temperature during rotation. The highest average lithium surface temperature was 51°C. FIG. 8B is a pressure map for the petal 804, showing that the pressure drop for the water flow of 0.002 m$^3$/s (32 gal/min) was 2 bar (29 psi). The pressure drop is a function of the desired flow rate and the restriction of the micro-channels. The greater the flow, or the smaller the channels, the more pressure from inlet to outlet that is required to achieve that flow. Also, when the rotatable structure is rotating, the actual pressure at the periphery of the disk is increased due to the centrifugal force applied to the coolant. The pressure differential and corresponding flow rate, however, are the same.

Figure 8C:
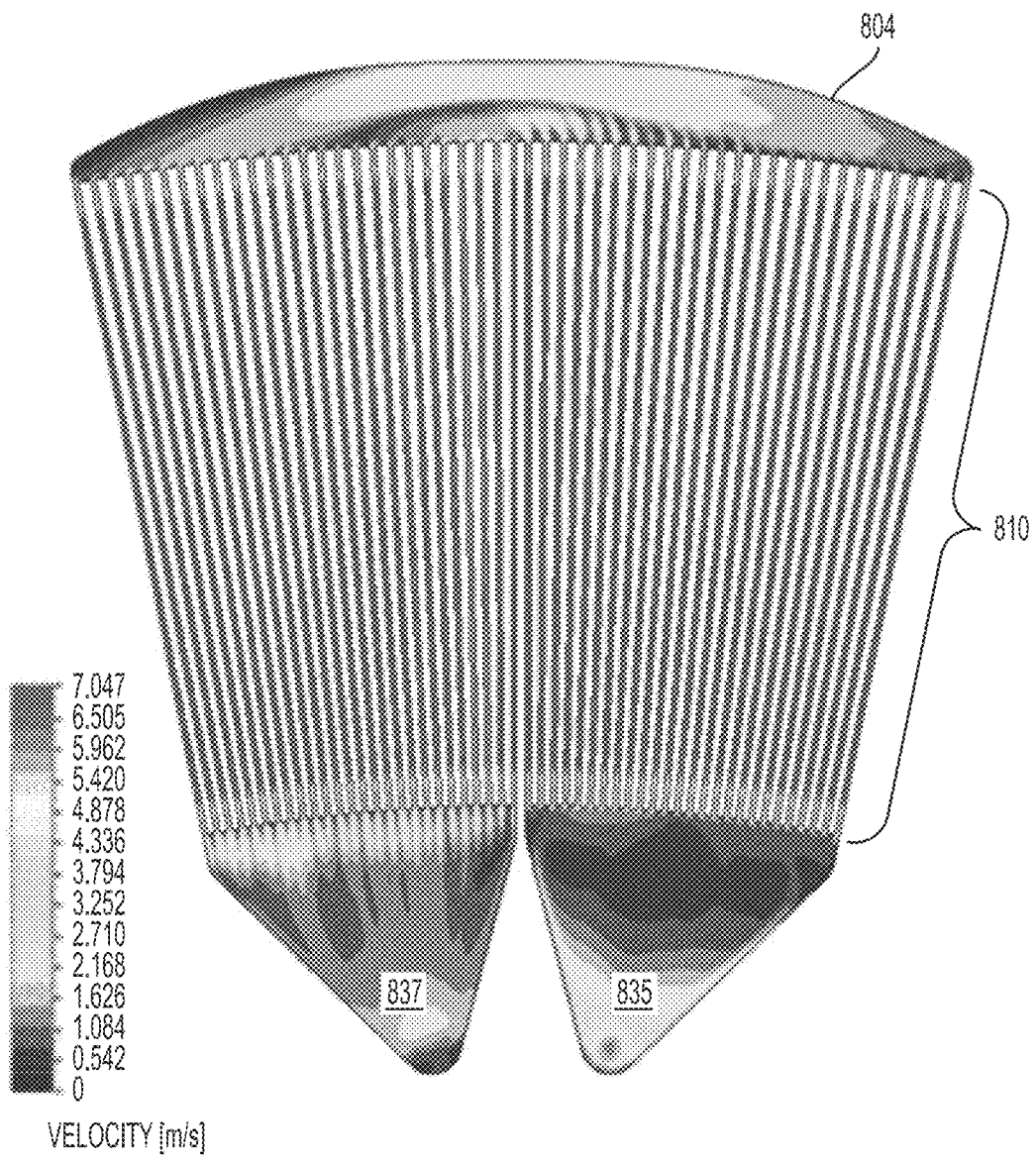
FIG. 8C is a map of micro-channel velocity for the micro-channel arrangement of FIG. 8A.
Figure 8D:
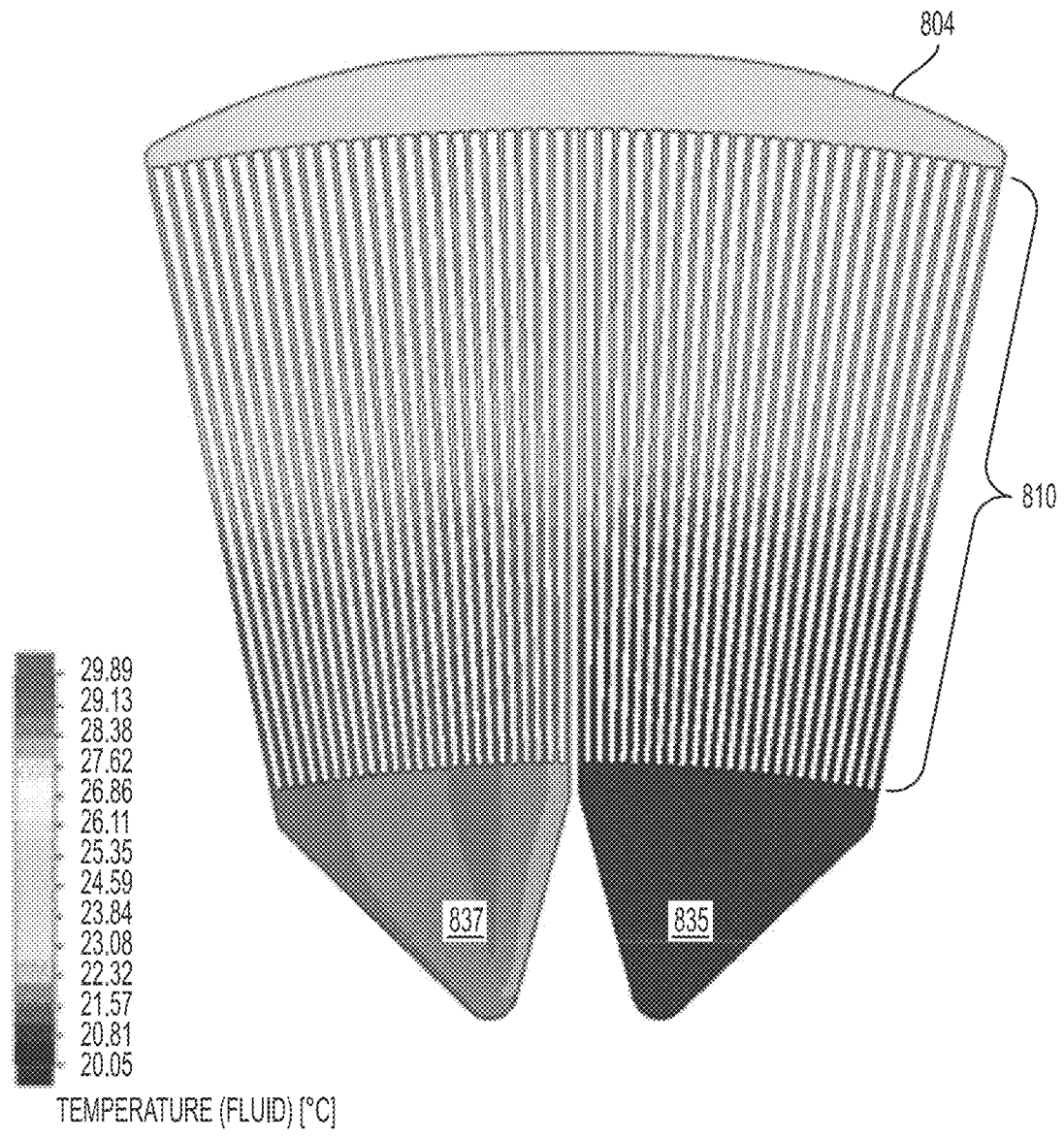
FIG. 8D is a thermal map, showing temperature change from the inlet to the outlet, for the micro-channel arrangement of FIG. 8A.

FIG. 8C is a map of micro-channel velocity for the petal 804, and FIG. 8D is a thermal map, showing the coolant temperature change from the inlet to the outlet, for the petal 804. The temperature rise from left to right, visible in FIG. 8D, extends to the surface, as can be seen in FIG. 8A, where the center left edge is hotter than the center right edge. Improvements over traditional designs include increased water flow (higher pressure), increased spin speed (up to 30 Hz, 1800 RPM), and a flatter beam profile (compared with Gaussian).

In some implementations, a neutron target with a centerline diameter of ¢ 84 cm is struck by 30 mA of 2.6 MeV protons ($1.9\times10^{20}$ ions/sec). Assuming a proton beam distribution of $\sigma=2$ cm, the centerline dose rate of $1.4\times10^{14}$ ions/cm$^2$/s yields a peak or maximum deposited dose (at the centerline of the beam on the petal) of $5\times10^{19}$ ions/cm$^2$ in 100 hours. Since this dose is well within the acceptable dose limit of protons on solid lithium, target lifetimes in excess of 100 hours are easily achieved.

Figure 9:
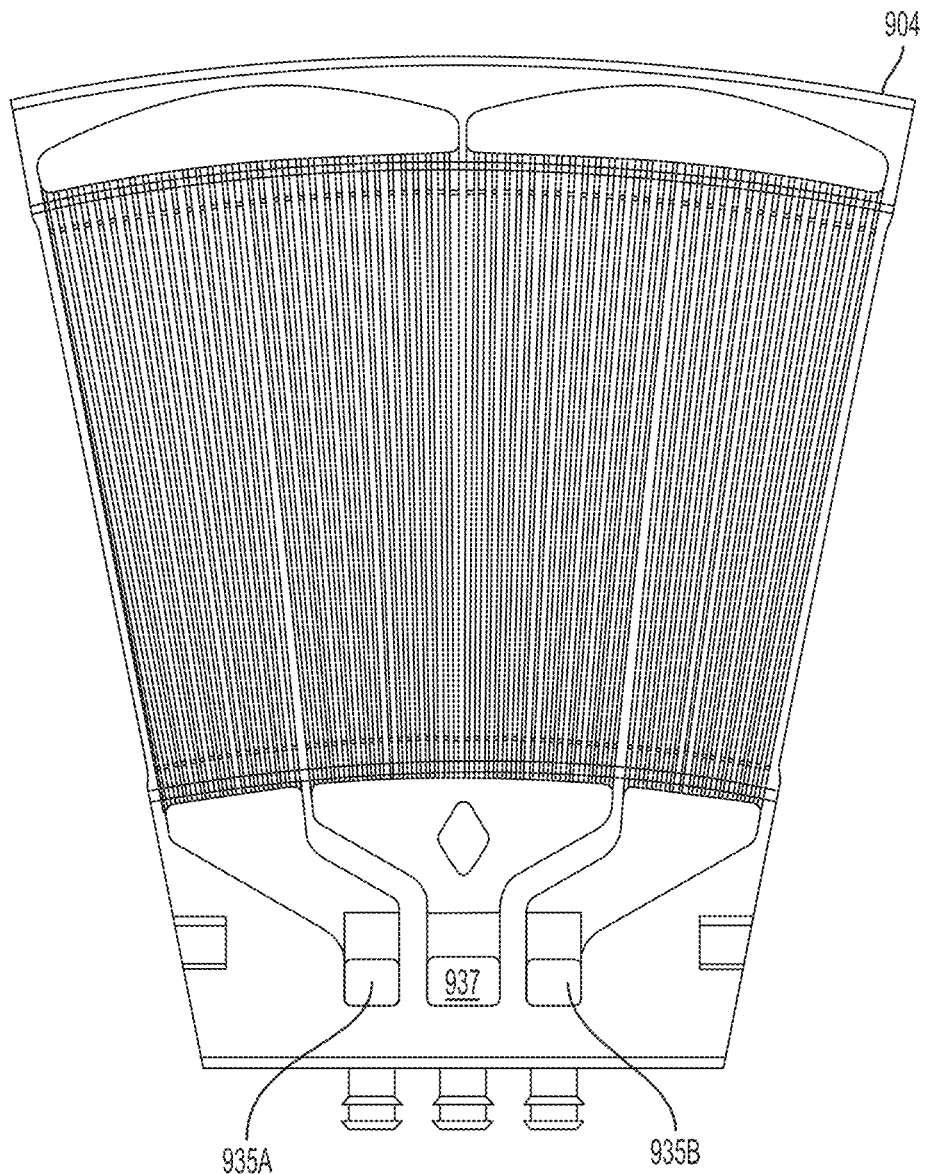
FIG. 9 is a rendering of a dual-inlet micro-channel arrangement, in accordance with some embodiments of the present disclosure.

A refinement on the petal embodiment shown in FIGS. 8A-8D can include two inlets of cold water on the petal 804 edges instead of one where the respective flows are routed so as to return to a common/central return cavity, thereby routing the hot water away from the edge of the petal and, correspondingly, improving the thermal budget. This configuration is shown schematically in FIG. 9. FIG. 9 depicts a petal 904 with two inlets 935A, 935B, an outlet 937.

During bombardment of the petals, i.e., when the protons enter solid lithium, they decelerate, releasing heat and other particles, such as neutrons, to a degree that is proportional to their energy loss until they come to rest approximately 250 µm deep in the solid lithium. In some implementations, an accelerator source produces proton beams of up to 100 kW in power (40 mA at 2.6 MeV). To accommodate such power, the beam diameter can be sized to be about 110 mm to 120 mm full width (6σ) at the target or petal surface, resulting in an average power density of about $1\times10^7$ W/m$^2$ in the beam and a peak of the 2D Gaussian distribution that is much higher, e.g., about $6\times10^7$ W/m$^2$. This is the flux that the lithium sees when the proton beam is striking it, which may be referred to as the "instantaneous" heat flux. Averaging over the rotatable structure, the beam centerline diameter multiplied by the "height" of the beam yields the swept area. For a beam centerline of 840 mm, this yields an average flux of about $4\times10^5$ W/m$^2$ with a peak flux on the centerline of about $8\times10^5$ W/m$^2$.

The average heat flux can be changed by making the rotatable structure bigger or smaller. A smaller rotatable structure will have more heat to dissipate per unit area on average, while a larger rotatable structure will have less heat to dissipate per unit area. The spin speed is also an important aspect of the rotatable structure design. The slower the rotatable structure spins, the larger the temperature spike as the proton beam passes over the petal. The faster the rotatable structure spins, the smaller the temperature spike. For a spin speed of 600 RPM, the temperature spike on the centerline of the Gaussian is approximately 60° C, and for 1,200 RPM it is approximately 30° C. It should be noted that, unlike in stationary configurations (not including scanned or restored beams), thermal effects on rotatable structures described herein include a transient component. In other words, when the beam passes over the petal the temperature will spike and then decay as disk rotates.

Figure 10:
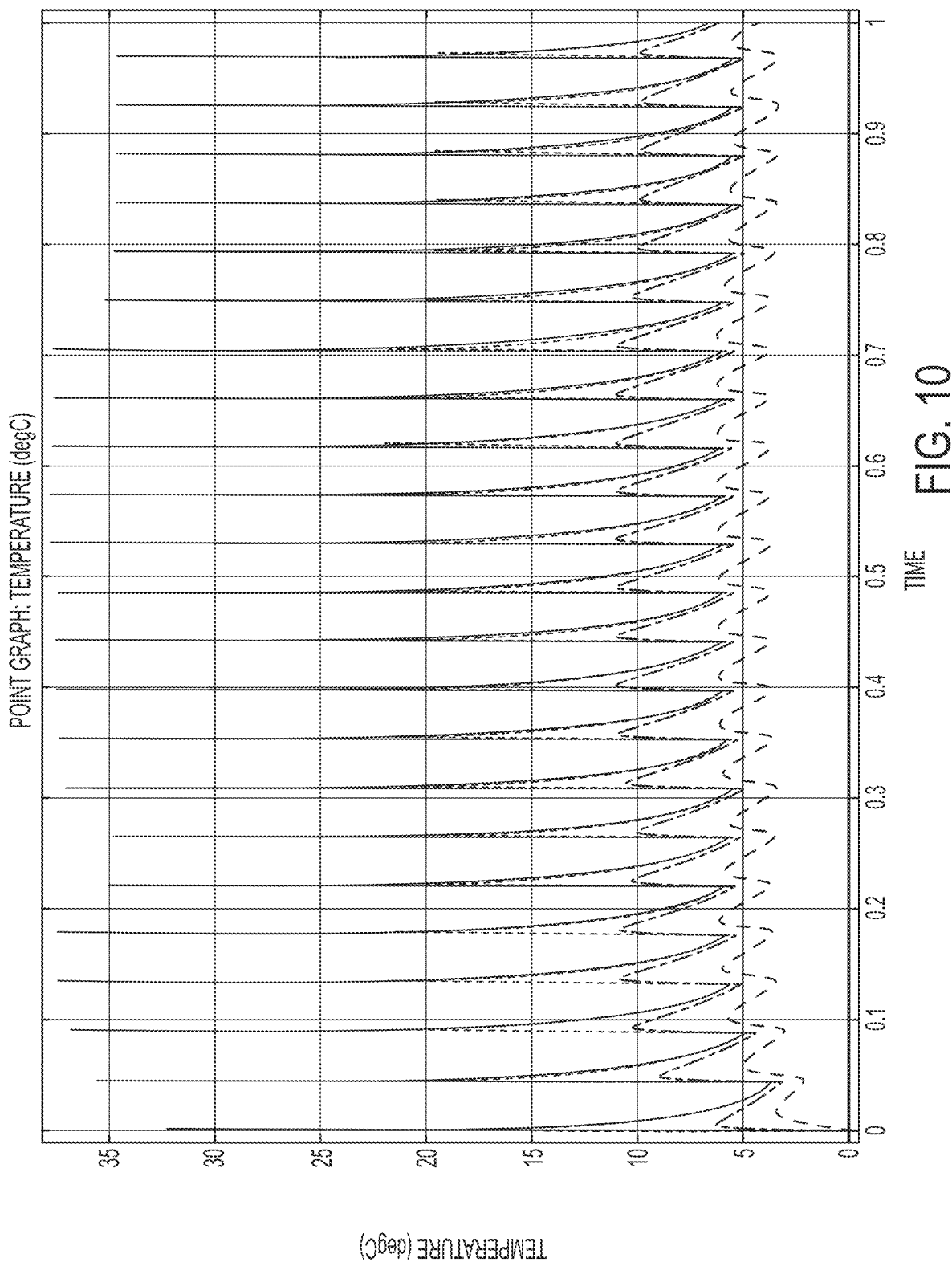
FIG. 10 is a plot of temperature over time during use of a BNCT system, in accordance with some embodiments of the present disclosure.

FIG. 10 shows the temperature delta/deviation from steady state as a proton beam passes across the petals. The highest line is at the centerline of the beam at the surface of the lithium. As can be seen, for the given parameters (i.e., a rotation speed of 1,200 RPM and a beam diameter of 12 cm+/−3σ, with a total power of 78 KW (2.6 MeV, 30 mA)), the transient temperature variation is about 35° C. to 40° C. with an average temperature of about 10° C. This transient from the average of 25° to 30° C. is in addition to the average surface temperature peak. Thus the maximum surface temperature seen by the solid lithium is the sum of the steady state and transient solutions, that is 51° C+30° C.=81° C. It should be noted that this is strongly dependent on spin speed, total power, and beam diameter.

Figure 11:
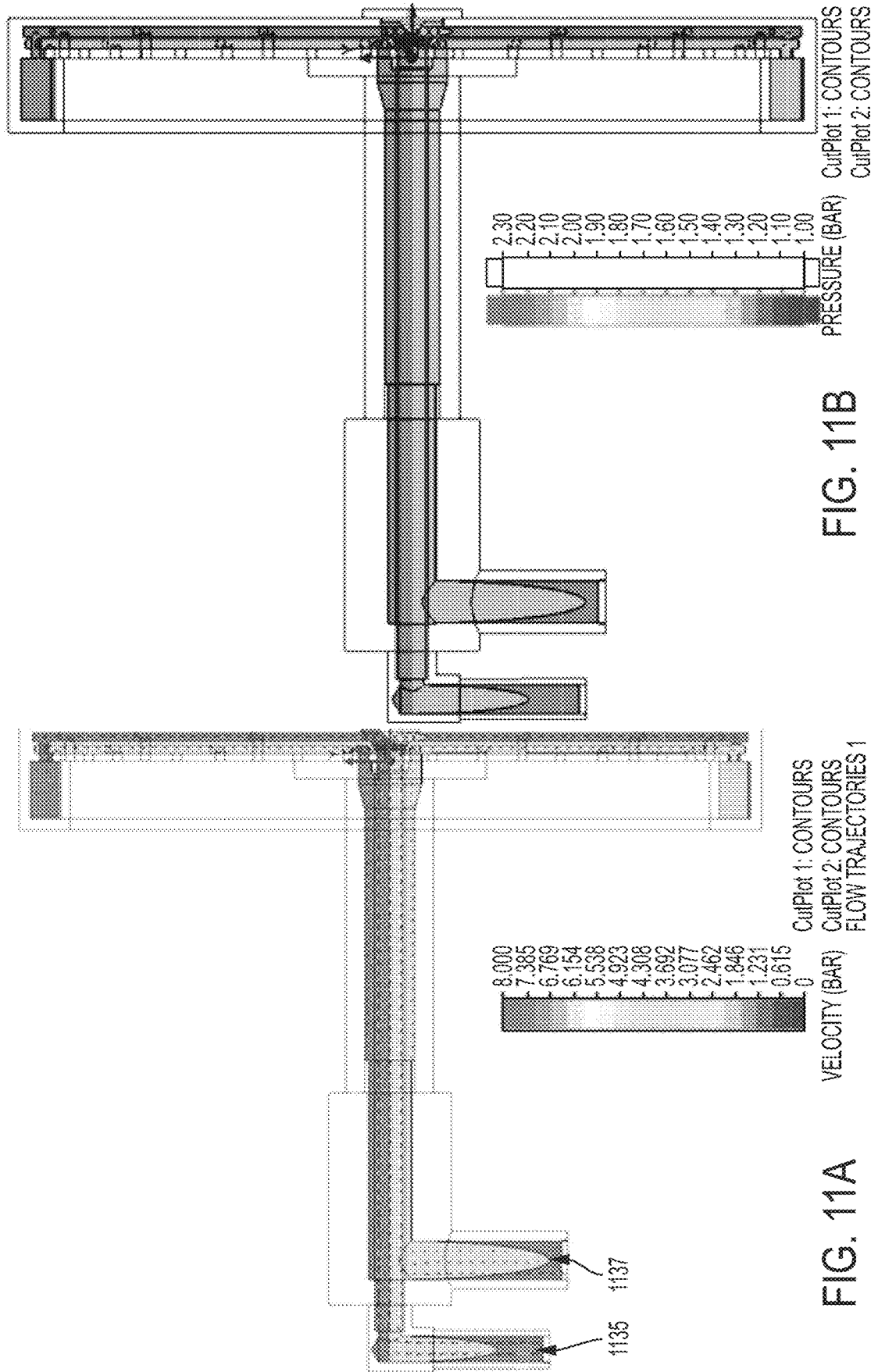
FIG. 11A is a rendering of a side-view of a rotatable target assembly, mapping coolant velocity, in accordance with some embodiments of the present disclosure.
FIG. 11B is a rendering of a side-view of the rotatable target assembly of FIG. 11A, mapping pressure.

FIG. 11A is a rendering of a side-view of a rotatable target assembly, mapping coolant velocity, in accordance with certain embodiments, and FIG. 11B is a rendering of a side-view of the rotatable target assembly of FIG. 11A, mapping pressure. The total pressure needed across the target assembly to achieve the calculated flow is the sum of the spindle/hub delta pressure and the petal delta pressure, that is 2 bar+1.3 bar=3.3 bar (48 psi). FIG. 11A shows a peak water velocity of 8 m/s and an inlet 1135 and outlet 1137. FIG. 11B depicts a pressure drop across the spindle of 1.3 bar.

An advantage of target designs described herein over other solid lithium is that the larger effective lithium surface area can accommodate higher powers than are possible on stationary targets. The equivalent circular diameter of cooling area for a rotatable structure as defined herein and having a 12 cm beam diameter on a 84 cm centerline, would be 63.5 cm in a stationary configuration, which is too large for practical BNCT designs. Also, the segmented architecture is convenient from a service perspective, as well as from a manufacturing perspective, since the application of the lithium can be performed in smaller increments (e.g., about 10 cm×about 10 cm). The larger effective lithium surface area of embodiments described herein also means that, as compared with other solid configurations, the lifetime is much longer, e.g., by an amount that is proportional to the ratio of surface areas. Also when compared to stationary targets, the petals can be robotically exchanged more readily and without disturbing the beam shaping assembly (BSA).

Rotatable structures of the present disclosure allow for straightforward beam positioning and intensity measurements during irradiation, for example using a faraday cup behind the rotatable structure and a series of holes or slots at various points around the rotatable structure. Such information is useful for beam tuning and safety interlocking of the system. Also, when compared to liquid lithium targets, rotatable solid structure offer the same safety benefits as the stationary targets. Petals of the rotatable structures are also more readily exchanged by a robot than a stationary target would be, since the beam shaping assembly (moderator) can stay in position.

ADDITIONAL EMBODIMENTS

The system described above for the $^7$Li (p,n)→$^7$Be can be extended to other neutron producing reactions with other neutron producing materials. In addition to the "near threshold" approach using a 1.9 MeV proton beam and the "above threshold" approach using a 2.5 MeV proton beam on lithium, other reactions that have been proposed for BNCT include: $^9$Be(p,n) using a 4 MeV proton beam, $^9$Be(d,n) using a 1.5 MeV deuterium beam, and $^{13}$C(d,n) using a 1.5 MeV deuterium beam. To utilize these reactions, a solid sheet of beryllium could be thermally bonded to the petals in place of the lithium and bombarded with either 4 MeV protons or 1.5 MeV deuterons. In addition, the lithium could be replaced with thin sheets of graphite or carbon to produce neutrons using the $^{13}$C(d,n) reaction.

A system of the present disclosure can include a rotatable structure, such as a platform or stage, with a neutron source material disposed thereon, and a proton beam generator configured to direct a proton beam at the neutron source material on the rotatable structure as it rotates about an axis of rotation, thereby generating neutrons. The neutron source material can be any neutron generating material, for example lithium, and can be positioned anywhere on the rotatable structure via a technique that depends, for example, on the type and form of the source material and the design of the rotatable structure. In some embodiments, the rotatable structure comprises neutron source material positioned on an exterior, outwardly facing surface of the rotatable structure that can be readily exposed to the directed proton beam.

The rotatable structure is rotatable about an axis of rotation and can have a variety of different overall shapes, such as disk-shaped (including circular), annular, or cylindrical, depending, for example, on the overall system design requirements. In some implementations, the rotatable structure is symmetrical, having an axis of rotation perpendicular to and in the center of the structure. The rotatable structure may be contained within an exterior housing, as desired, depending on the application. In addition, the rotatable structure may be formed using a variety of different materials, depending, for example, on the chemical reactivity of the neutron source material, the conditions needed to contain the source material in its desired form, and cost. For example, the rotatable structure may include stainless steel or molybdenum.

The rotatable structure can include a base that is substantially flat but may further include various additional components or features, as desired, in order to, for example, contain a solid and/or liquid form of the neutron source material. The base may further include a means for rotation, such as a motor and axel. In some embodiments, the base can include a central rotatable hub comprising various means of delivering heat transfer agents, such as heating fluids or coolants, to various portions or components of the base and/or of the rotatable structure. Channels can also be provided in the base as well as in various components of the rotatable structure to assist in delivering these fluids. Furthermore, the base may include at least one neutron source material containment section which is configured to hold the neutron source material in a targeted position. The shape, size, location, and number of containment sections can depend, for example, on the type and form of the neutron source material, the method in which the source material is provided onto the base, and/or the design of the rotatable structure.

In some embodiments, the rotatable structure is a disk-shaped structure having a base comprising a rotatable hub that is centrally positioned within the base. The base also can include at least one base segment having an outwardly-facing exterior surface configured to contain and/or carry the neutron source material. The neutron source material can include a layer of solid neutron source material, such as lithium. The hub can include at least one coolant line extending to the at least one base segment. The proton beam generator is configured to direct the proton beam at the neutron source material contained by or carried on the base segments. In some embodiments, the disk-shaped structure is rotatable about an axis of rotation, and the proton beam can be directed along a beam path that is substantially parallel to the axis of rotation.

In some embodiments, the rotatable structure is a cylindrical structure having a base (e.g., a horizontal base) that is connected to a substantially perpendicular outer wall (e.g., a vertical outer wall). The outer wall can include at least one wall segment having an inwardly-facing exterior surface that is configured to contain a film of a liquid neutron source material, such as liquid lithium, and the proton beam generator can be configured to direct the proton beam at the film of liquid neutron source material contained on the wall segments. The cylindrical structure is rotatable about an axis of rotation, and the proton beam can be directed along a beam path that is substantially perpendicular to the axis of rotation.

In some embodiments, a method of generating neutrons can use of any of the rotatable structure embodiments described herein. For example, a rotatable structure comprising a neutron source material can be provided. The rotatable structure can be rotated about an axis of rotation, and a proton beam generated by a proton beam generator can be directed at the neutron source material as it rotates, thereby generating neutrons.

In some embodiments, the rotatable structure includes a disk-shaped structure having a base and a rotatable hub centrally positioned within the base, the base can include at least one base segment with an outwardly-facing exterior surface having a layer of solid neutron source material. The hub can include at least one coolant line that extends to the at least one base segment. As the disk-shaped structure is rotated about an axis of rotation, a proton beam generated by a proton beam generator is directed at the layer of solid neutron source material along a beam path, for example a beam path that is substantially parallel to the axis of rotation, such that neutrons are generated upon interaction between the proton beam and the solid neutron source material.

In some embodiments, the rotatable structure can be a cylindrical structure having a base that is connected to a substantially perpendicular outer wall, the outer wall can include at least one wall segment having an inwardly-facing exterior surface that is configured to contain a film of a liquid neutron source material. A solid neutron source material can be provided on the base, and liquid neutron source material can be formed by melting the solid neutron source material. As the cylindrical structure is rotated about an axis of rotation, liquid neutron source material can flow from the base to the inwardly-facing exterior surface of the wall segment, thereby forming the film of liquid neutron source material. A proton beam generated by a proton beam generator can be directed at the film of liquid neutron source material along a beam path, for example a beam path that is substantially perpendicular to the axis of rotation, such that neutrons are generated upon interaction between the proton beam and the liquid neutron source material.

It is to be understood that the foregoing general description and the following detailed description are exemplary and explanatory only. Those skilled in the art may make various modifications and additions to the processes of the present disclosure without departing from the scope of the present disclosure.

In some embodiments, the rotatable structure includes a base having at least one base segment that includes the neutron source material, which can be a solid. The base may be positioned vertically or horizontally, for example based on the configuration and position of the proton beam generator. The overall shape of the rotatable structure can vary, and in some embodiments is disk-shaped, with a base that is annular, circular, or nearly circular (i.e., having a polygonal shape approximating a circular disk). The rotatable structure can be symmetrical, having an axis of rotation perpendicular to and in the center of the base. The base can be substantially flat, or can comprise an annular stepped or angled region comprising base segments. The base segments can also be substantially flat.

The "base segment" of the rotatable structure can refer to any portion within or on the base and can include, for example: (1) an outwardly-facing exterior surface (i.e., facing towards the proton beam generator) that is configured to contain the neutron source material, and (2) a layer of solid neutron source material, such as lithium. The base can be divided into a plurality of base segments that are separated, for example, by raised separators, or the base and its segments can form one continuous surface. In some embodiments, the rotatable structure has a circular base comprising annular base segments or comprising pie-shaped or partial pie-shaped base segments. In this way, the exterior surface may comprise one continuous layer of neutron source material or may include layers positioned in various targeted segments or sections along the exterior outwardly-facing surface. The exterior surface of the base segment can be disposed such that a major surface thereof is perpendicular to the proton beam that is generated by the proton beam generator and directed at the neutron source material. However, the segments may be tipped or angled in order to increase the surface area of the solid source material that becomes contacted by the proton beam. Alternatively, the beam itself can be directed to strike the neutron source material at an angle, thereby increasing the contacted area.

The rotatable structure can be formed using a variety of different materials, depending, for example, on the chemical reactivity of the neutron source material, the conditions needed to produce the layer of solid source material, and cost. For example, the rotatable structure may comprise stainless steel or molybdenum. The base segments can include one or more high conductivity materials, such as copper, aluminum, or molybdenum. The solid layer of source material can be provided on the exterior surface of the base segments by depositing or coating the solid source material directly thereon. Alternatively or in addition, preformed layers can be placed or positioned directly onto the exterior surface of the base segments. In some embodiments, the exterior surface also includes one or more neutron source material containment sections, and solid neutron source material, in non-layer form (such as flakes, pieces, or pellets) may be provided within these sections, melted, and cooled to form the layer of solid source material. While the solid source layer may be provided directly onto the base segment surface, one or more intermediate layers may also be used, for example to improve bonding (and, correspondingly, the thermal contact) of the layer to the segment surface. This layer may also provide a physical barrier to prevent chemical interactions between the source material and to the segment. For example, for a solid lithium target, an intervening layer of copper may be used to provide improved bonding of the lithium target to an aluminum base segment while preventing amalgamation of the aluminum by the lithium. Intermediate layers may also be used to increase the dose threshold of blistering in the target. When exposed to high influences of protons, most materials eventually blister due to the accumulation of hydrogen gas and damage at the end of range of the particles in the material. If the thickness of the source material is chosen to be less than the range of the protons in that material, then the protons will stop, or "brake," in a deeper layer. This deeper layer may be made of a material that is resistant to blistering, such as iron, tantalum, or others known in the art. This blister stop layer may include a bonding or barrier layer, or may be in addition to any bonding or barrier layers. The thickness of the solid layer of source material can vary, depending, for example, on the targeted application, the power of the proton beam, and the exposure time of the layer. For example, the solid layer can be 2 mm in thickness or less, from about 0.1 mm to about 1 mm, or from about 0.05 mm to about 0.5 mm.

In some embodiments, the base includes a rotatable hub that is centrally positioned within the base, along with various means of delivering heat transfer agents, such as heating fluids or coolants, to various portions of the base. For example, the base can include at least one coolant line extending from a central rotatable hub unit to the base segment, which includes the solid neutron source material. In this way, coolant can be delivered to cool the outwardly-facing exterior surface of the base, such as through channels provided therein that enable thermal communication of the coolant with the exterior surface while the proton beam is focused and reacting with the layer of solid neutron source material.

Liquid Neutron Source Material

In some embodiments, a rotatable structure includes a base connected to an outer wall, and the outer wall includes the neutron source material. The rotatable structure can be symmetrical, with an axis of rotation that is perpendicular to, and in the center of, the base. The overall shape of the structure can be cylindrical or substantially cylindrical, comprising a base connected to a substantially perpendicular outer wall. For example, the rotatable structure can be a horizontal base, such as a circular base, that is connected to a vertical or substantially vertical wall along its outer circumference.

The outer wall of the rotatable structure can include an inwardly-facing exterior surface (i.e., facing towards the center of the base) that is configured to contain the neutron source material, such as a film of a liquid neutron source material, e.g., lithium. A variety of different techniques can be used to contain the film, several of which are described below. In addition, the outer wall may be angled or tipped a few degrees (such as 1-2 degrees) outwardly from vertical (i.e., away from the center of the base) and therefore may not be precisely parallel with the axis of rotation, for example to assist in formation of the film of the liquid neutron source material.

In some embodiments, the outer wall of the rotatable structure is a continuous circular ring, having one continuous inwardly-facing exterior surface, or is segmented into a plurality of distinct wall segments, thereby separating the inwardly-facing exterior surface into various sections configured to each contain a film of a targeted amount of the liquid neutron source material. For example, the outer wall may include a plurality of wall segments, each having a similar shape and size. The wall segments may have a curved shape, forming arc segments of the overall circular cross-sectional shape of the outer wall, or may be flat, thereby approximating the overall circular ring shape of the outer wall. The inwardly-facing exterior surface of the outer wall can be segmented into wall segments using a variety of methods, including, for example, by providing raised separators attached to the exterior surface of the outer wall, by forming indented pockets or depressions within the outer wall, or by physically separating and dividing the outer wall into detachable wall segment pieces.

The base of the rotatable structure is preferably contiguous with the outer wall. Thus, the base and wall may be formed as one unit or, alternatively, may be separate components connected or bonded together. The base can have a variety of different shapes, such as annular, circular, or nearly circular (having a polygonal shape approximating a circle). In some embodiments, the base is generally flat and comprises a rotatable hub that is centrally positioned within the base, as well as various means of delivering heat transfer agents, such as heating fluids or coolants to various portions of the base and/or the outer wall. For example, the base can include at least one coolant line extending from a central hub unit to one or more wall segments of the outer wall, thereby delivering coolant to cool the inwardly-facing exterior surface of the outer wall, such as through channels provided therein that enable thermal communication of the coolant with the exterior surface.

In some embodiments, the base further includes at least one neutron source material containment section, such as a trough or well, in which a solid neutron source material, such as lithium, is placed and held, for example as the base is rotated. The volume of the trough can be greater than the volume of the neutron source material to be positioned therein, and, as such, be sufficient to contain the source as a melt. The total volume of all containment sections can be selected so as to be sufficient to hold the total volume of source needed to produce the desired neutron beam. The trough(s) can be located anywhere within or on the base, for example at the junction between the base and the outer wall, thereby permitting fluid communication between the trough and the outer wall. While one continuous trough or well can be used, a plurality of troughs can also be provided, in which case each trough can be separated from a neighboring trough by a raised separator or divider. In this way, liquid neutron source material formed within the trough or well can be contained in discrete portions at specific locations along the base, for example at the junction between the base and the outer wall. In some embodiments, when the base includes a plurality of troughs, the outer wall also includes a plurality of corresponding wall segments, with each trough being in fluid communication with one or more wall segments. Thus, the discrete portion of liquid neutron source material will be in fluid communication with a wall segment having an interior surface which is configured to contain a film of the source material.

When the base comprises one or more troughs, the base can also include at least one feeder line extending from a central hub unit to one or more of the troughs, thereby delivering heat transfer fluid to heat and melt solid neutron source material positioned in the trough, such as through channels provided in the base near or beneath the trough to enable thermal communication of the fluid with the trough. In this way, the neutron source material can be converted to a liquid form. Alternatively, the system can include at least one heat source, such as one or more internal heaters or heat lamps that are positioned and configured to heat the solid neutron source material. Such heating can be applied to one trough at a time or to all troughs simultaneously, for example by rotating the structure, as desired to form the liquid neutron source material. In addition, the proton beam to be directed at the film of neutron source material, generated as discussed below, may be re-directed onto the trough, with the beam power being used to assist in initiating the melting of the neutron source material.

In some embodiments, the rotatable structure is formed using one or more of a variety of different materials, depending, for example, on the chemical reactivity of the neutron source material, the conditions needed to contain the source material in liquid form, and cost. For example, the rotatable structure may comprise stainless steel or molybdenum. Surprisingly, in the present disclosure, the ability of the liquid neutron source material to wet the material used to form the rotatable structure material is not necessary. Without wishing to be bound by theory, the inventors note that lithium has a relatively high surface tension (approximately 400 dynes/cm at 200° C.) and a relatively low density (approximately 0.5 $g/cm^2$), which leads to a very high tendency of lithium to "ball-up" or contract into thick puddles on a flat surface, making it challenging to create a thin, uniform film of liquid lithium. To address this problem, rotatable structures described herein can be formed with a material that is readily wetted by lithium. However, this would make it more challenging to remove unused or spent lithium for replacement or system maintenance. In some embodiments of the present disclosure, materials that are not well wetted by lithium at the desired operating temperatures (such as below 300° C.) can be used, providing both economic and functional advantages.

As noted above, in some embodiments a system can include a proton beam generator. Any source of a proton beam can be used, including, for example, a proton beam generator comprising a proton accelerator, and selection of the proton beam source can depend, for example, on the proton beam target and/or the desired application of the resulting neutron beam. For clinical BNCT, the energy range of neutrons required is between 1 eV and 10 keV. For the "above threshold" approach using a ~2.5 MeV proton beam, the average energy of the neutrons produced is about 600 keV. The total energy range is between thermal and 2.5 MeV neutrons, but there is a strong peak in the cross-section at 600 keV. Thus, the neutrons should be "moderated" (i.e., slowed down) to the epithermal range by filtering them through an array of materials and thicknesses. For example, for neutron production from a lithium target ($^7Li(p,n)^7Be$), the reaction requires a source of protons with an energy from at least 1.88 MeV to about 2.4-2.7 MeV. A high current proton accelerator is preferred, such as a proton accelerator operating with a proton current of 30-50 mA and a proton energy of 1.9-2.7 MeV. The proton beam from the proton beam generator can be focused on neutron source material (either as a liquid film or solid layer, as described above), thereby generating neutrons.

Furthermore, in embodiments of the present disclosure, the beam can be monitored and profiled during neutron production. The rotatable structure can be segmented in the circumferential direction such that there are many depressions each containing a film or layer of lithium. A single, small hole can be drilled in the base segments or vertical outer wall between each pair of depression such that the plurality of holes would form, for example, a helical pattern on the inside of the outer wall. A faraday cup can be placed behind the rotating structure such that the beam impinges on it when a hole passes in front of the beam. The data collected from the faraday cup, combined with timing information from the rotation structure can be used to reconstruct a two-dimensional profile of the beam at each revolution, without interrupting neutron production. This information can be useful in ensuring that the desired beam profile, location and intensity are maintained.

In some embodiments, a method includes providing a disk-shaped rotatable structure having a base with a centrally-positioned rotatable hub, the base comprising at least one base segment having an outwardly-facing exterior surface configured to contain a layer of solid neutron source material, such as lithium, and the hub comprising at least one coolant line extending to the base segments. As the disk-shaped structure is rotated about the axis of rotation, the proton beam provided by the proton beam generator is directed at the layer of solid neutron source material, thereby generating neutrons. The proton beam can be directed along a beam path that is substantially parallel to the axis of rotation.

In another embodiment, the rotatable structure is a cylindrical structure having a base that is connected to a substantially perpendicular outer wall. The outer wall can include at least one wall segment having an inwardly-facing exterior surface configured to contain a film of a liquid neutron source material, such as lithium. A solid neutron source material can be provided on the base, for example in one or more troughs or wells positioned at the junction between the base and the outer wall, permitting fluid communication between the trough and the outer wall, and liquid neutron source material can be formed by melting the solid neutron source material. As the cylindrical structure is rotated about the axis of rotation, liquid neutron source material flows from the base to the inwardly-facing exterior surface of the wall segment, thereby forming the film. The proton beam provided by the proton beam generator is directed at the film of the liquid neutron source material, thereby generating neutrons. For example, the proton beam can be directed along a path that is substantially perpendicular to the axis of rotation (e.g., forming an angle with the axis of rotation of from about 80° to about 100°, or from about 85° to about 95°)

The melting of the solid neutron source material can occur prior to or simultaneously with the rotation of the rotatable structure, depending, for example, on the speed of rotation and the relative rate of heating and melting of the source. For example, the rotational speed can be about 500 RPM, generating a centrifugal force of at least about 150 gs. The thickness of the liquid film can vary, depending, for example, on the targeted application, the power of the proton beam, and the exposure time of the film. The liquid film can be 5 mm in thickness or less (e.g., from about 1 mm to about 3 mm). Conditions for forming the film can depend upon the properties of the liquid source material and the exterior surface of the outer wall. Sufficient centrifugal force should be applied to the liquid source in order to produce a flat substantially continuous film having the desired thickness. For example, for a lithium source, a rotation frequency of approximately 600 RPM can be used, corresponding to a centrifugal force of approximately 200 gs, which is expected to be sufficient to produce a lithium film of approximately 1.25 mm in the case of a segment material that is not wetted by the lithium. Use of a volume of lithium sufficient to provide a thicker film, such as 2 mm thick, would ensure that the behavior of the puddle will not be dominated by surface tension, and will expand to cover the entire depression in the pedestal.

Figure 12:
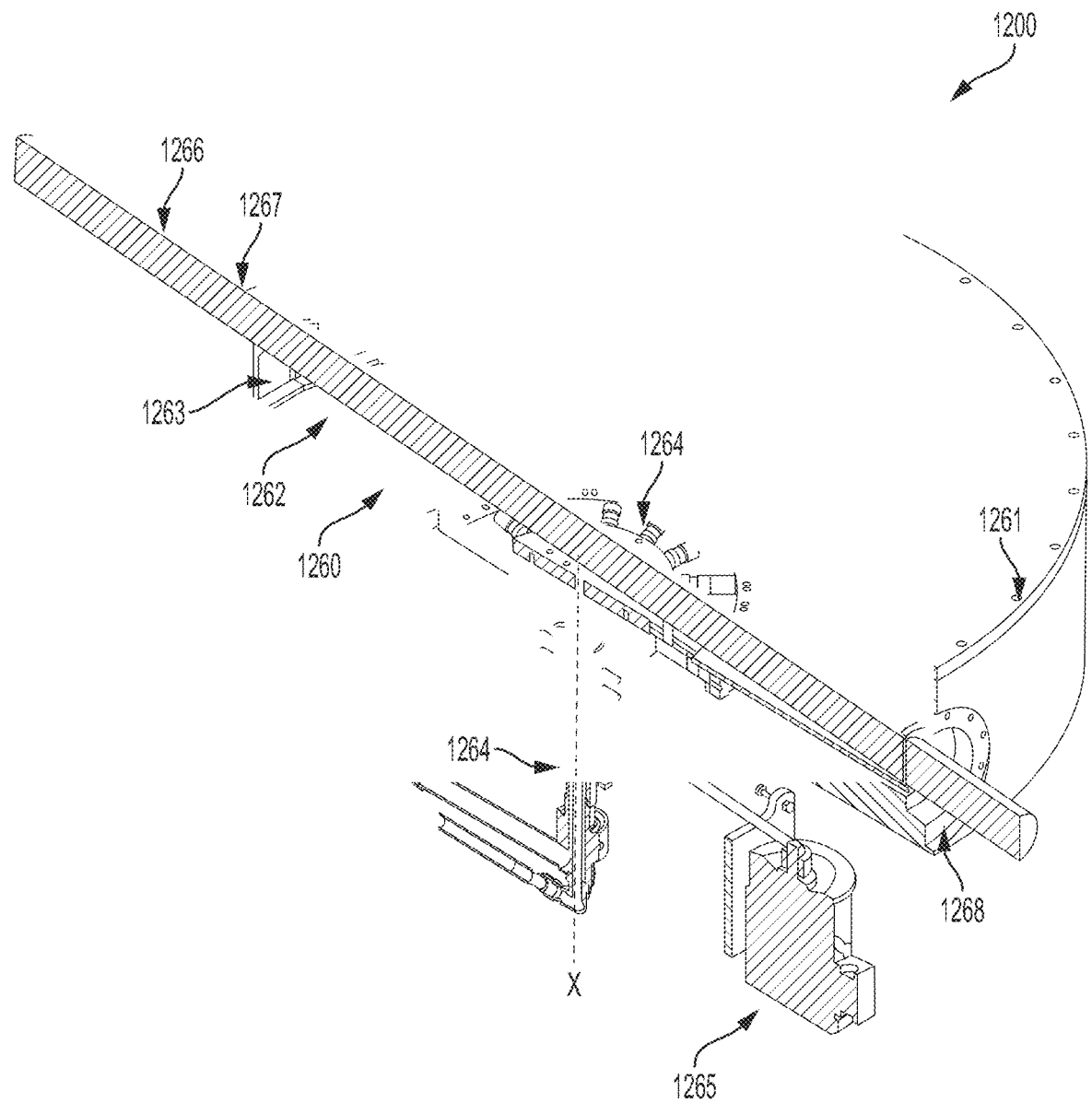
FIGS. 12 and 13 are schematic drawings of a rotatable cylindrical structure that can be used in BNCT systems described herein.

A specific example of one embodiment of a neutron generation system is shown FIG. 12. As shown, system 1200 includes rotatable structure 1260 having axis of rotation X contained within external housing 1261. Rotatable structure 1260 has an overall cylindrical shape and includes horizontal base 1262 connected to vertical outer wall 1263, which is segmented in a plurality of wall segments, which are more clearly seen in FIG. 13. System 1200 further includes rotatable hub 1264 centrally positioned within base 1262 that includes coolant lines and/or feeder lines for heat transfer fluids as needed. Motor 1265 rotates structure 1260. As shown in this specific example, proton beam 1266 enters structure 1260 through opening 1267, which is above the top edge of outer wall 1263 and passes on to the opposite side, striking the liquid neutron source film as it rotates past. Neutrons are generated and exit structure 1260 through aperture 1268. Thus, for this cylindrical structure, the proton beam is directed along a beam path that is substantially perpendicular to the axis of rotation, deviating slightly from perpendicular only by the height of outer wall 1263. Adding a slight outward tip of a few degrees may be desirable in order to assist in film formation, and would bring the beam path closer to perpendicular.

Figure 13:
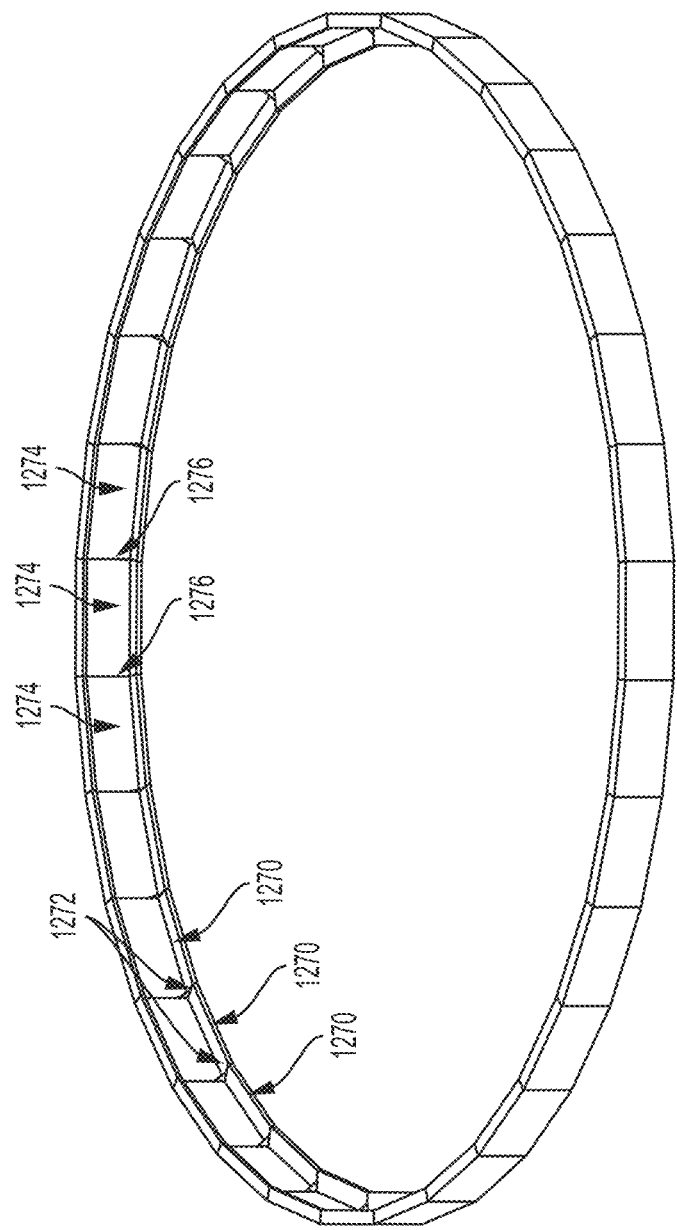

FIG. 13 shows further details concerning rotatable structure 1260. As shown, the horizontal base portion of structure 1260 is divided into a plurality of troughs 1270 by raised base separators 1272. In addition, an outer wall portion of structure 1260 is divided into a plurality of wall segments 1274 by raised wall separators 1276. As shown, each trough 1270 is positioned adjacent to a corresponding wall segment 1274 at the junction of the base and the outer wall.

Figure 14A:
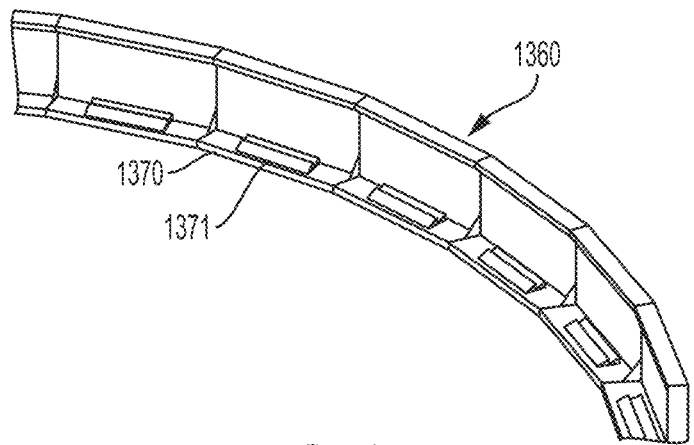
FIGS. 14A-14C show various stages of formation of a film of liquid neutron source, in accordance with some embodiments of the present.
Figure 14B:
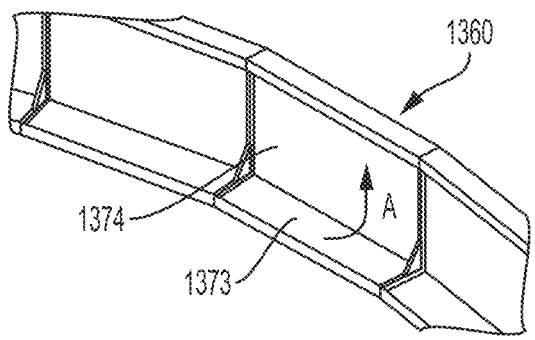
Figure 14C:
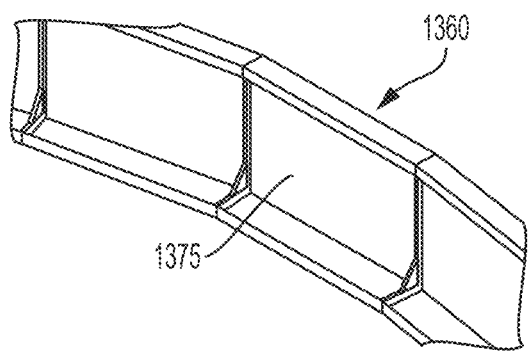

A specific example of the formation of a film of a liquid neutron source material, such as lithium, is shown in FIGS. 14A-14C. As shown in FIG. 14A, solid lithium 1371 in the form of tubes (although other forms and shapes are possible) is positioned within troughs 1370 of structure 1360. Heat is provided to the troughs, either through channels in the horizontal base connected to feeder lines in the central rotatable hub or by an internal heater, such as heat lamps, positioned near the troughs. As shown in FIG. 14B, heating melts solid lithium 1371 to produce liquid lithium 1373. Troughs 1370 have a volume higher than the volume of liquid lithium 1373, and thus the liquid neutron source material is contained therein. Simultaneously with the melting step, or subsequently, structure 1360 is rotated at sufficient speed to cause liquid lithium 1373 to climb up and into wall segments 1374 (indicated by arrow A) thereby forming liquid lithium film 1375 (shown in FIG. 14C). Wall segment 1374 is properly configured to contain film 1375, having the proper volume, surface properties, and separator heights for the given rotational speed and conditions.

A proton beam directed at the lithium film target as it rotates through the beam can produce the desired stream of neutrons, with the benefit of minimizing the volume of liquid lithium needed for the neutron source target while also avoiding the problem of blistering, expected for solid neutron targets or liquid targets that prematurely solidify. In addition, because the liquid source (i.e., lithium) does not need to flow, there is no significant concern if unintentional solidification does occur. In some embodiments, the lithium can be maintained at or below its melting point, operating as a two-phase system. Much of the beam energy would be absorbed by the phase change of the lithium, minimizing any temperature spike as the target passes through the beam. This would be expected to reduce the risk of boiling lithium, allowing operation at lower temperatures while still eliminating the problem of blistering. Furthermore, heat removal is improved compared to methods using a stationary target since the heat generated is spread over a large area as the target rotates, while also maintaining the neutron source in a small region, as is desirable for most applications. Additional heat removal can be provided by circulating coolant through coolant lines that extend from a central hub unit in the horizontal base to one or more wall segments of the outer wall, thereby delivering coolant to be in thermal communication with the inwardly-facing exterior surface of the outer wall, such as through channels provided therein. Also, heat transfer fluid used to melt the lithium may also be circulated to be in thermal communication with the inwardly-facing exterior surface, such as through connecting channels, maintaining the temperature of the liquid film.

Additional expected benefits of the present method and system include fast, robotic removal of the neutron source material for replacement or system maintenance. For example, a lithium target could be allowed to solidify in the trough of the horizontal base. If the trough is prepared using a material having a suitable anti-stick surface for lithium, pellets of lithium would form, which could be removed directly or, alternatively, a removable trough can be used. This would minimize downtime for maintenance or lithium replacement and would also significantly reduce the radiation hazard to maintenance personnel associated with the radioactive beryllium reaction product contained in the lithium. Additional benefits are also possible, given the benefit of the present disclosure.

Figure 15A:
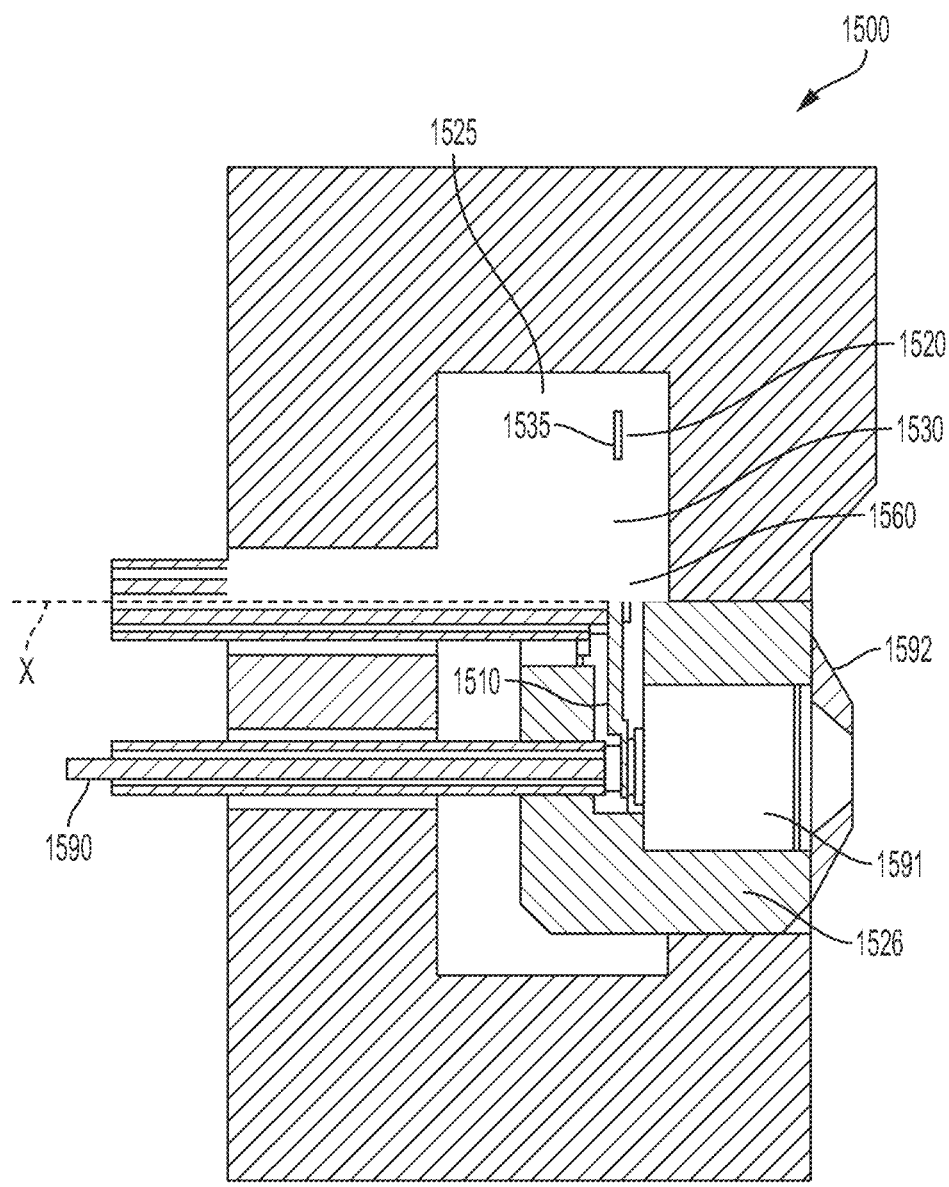
FIGS. 15A-15D show various embodiments of a rotatable disk-shaped structure, in accordance with some embodiments of the present disclosure.

A specific example of another embodiment of a neutron generation system of the present disclosure is shown FIG. 15A. As shown, system 1500 includes rotatable structure 1510 having axis of rotation X contained within external housing 1525 and surrounded by neutron reflector 1526. Rotatable structure 1510 has an overall disk shape and includes vertical base 1530 which has an annular stepped region comprising base segment 1520 upon which solid lithium layer 1535 is provided. Base 1530 further includes rotatable hub 1560 (only partially visible in FIG. 15A) and includes coolant lines and/or feeder lines for heat transfer fluids as needed to cool solid lithium layer 1535 while rotating. Rotatable structure 1510 is rotated about axis X, and proton beam 1590 strikes solid lithium layer 1535 as it rotates past, thereby generating neutrons, which exit through moderator 1591 and collimator 1592. Thus, for this disk-shaped rotatable structure, the proton beam is directed along a path that is substantially parallel to the axis of rotation.

Figure 15B:
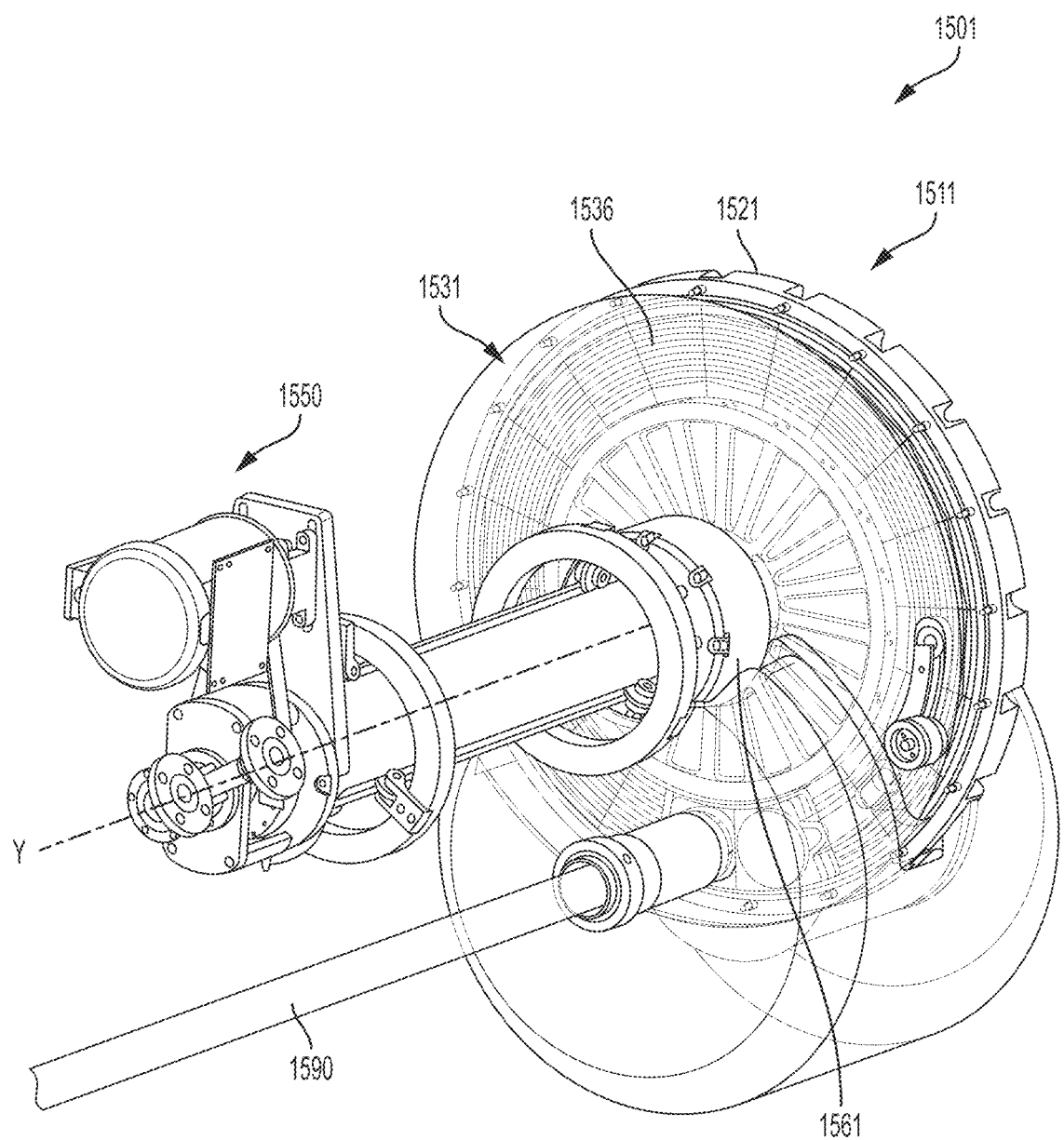
Figure 15C:
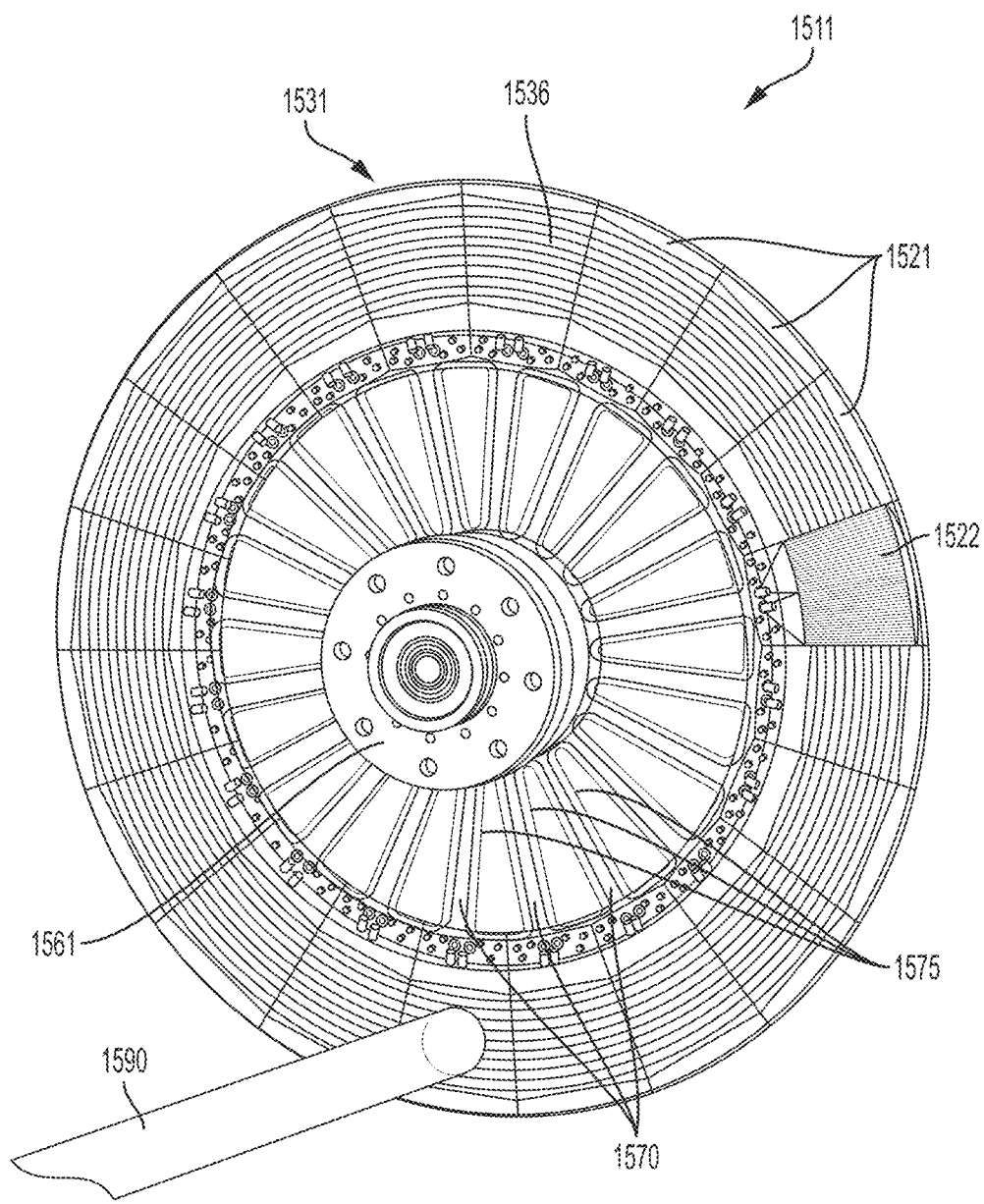
Figure 15D:
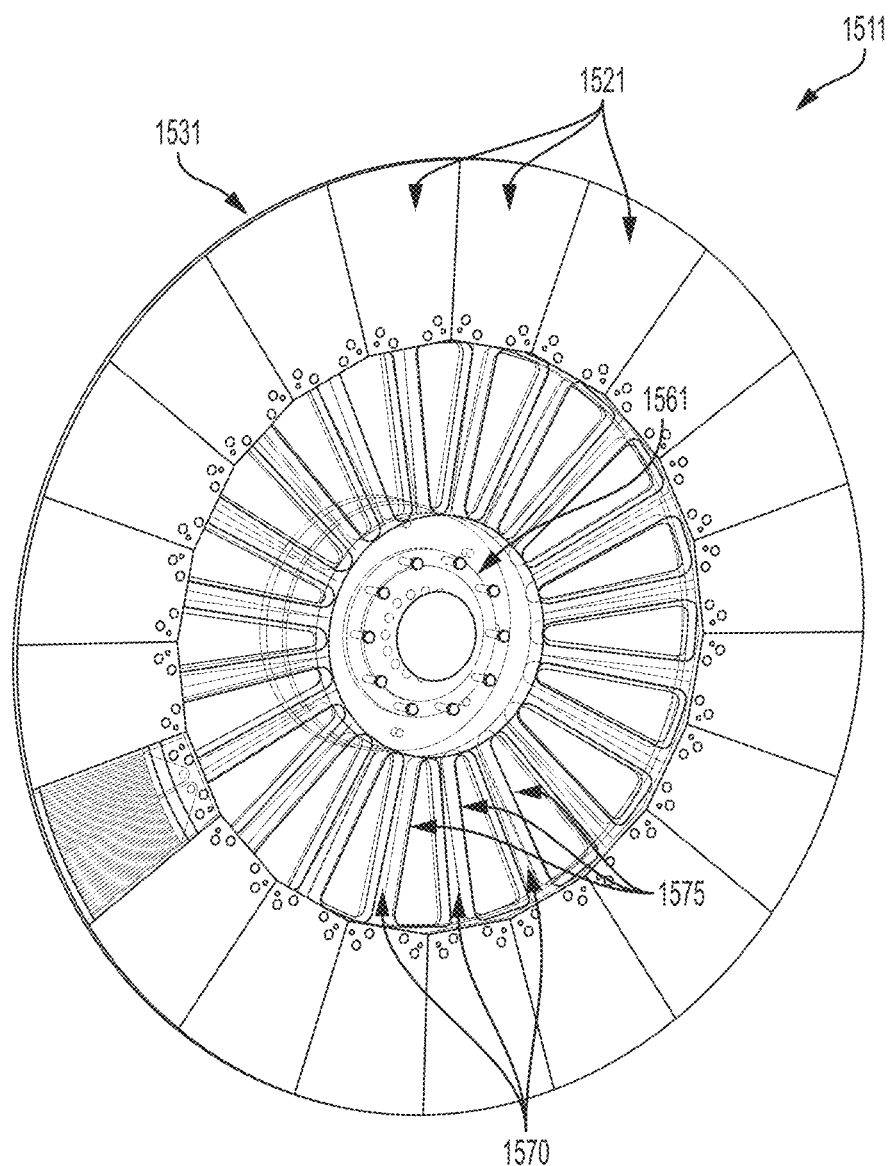

An additional specific example of this embodiment is shown in FIGS. 15B-15D. Regarding FIG. 15B, system 1501 is shown comprising rotatable structure 1511 having an overall disk shape, which further includes vertical base 1531 having base segments 1521 upon which solid lithium layer 1536 is provided. This is more clearly seen in FIG. 15C, which is a front view of rotatable structure 1511. Base 1531 includes rotatable hub 1561 which includes a plurality of coolant lines 1570 and feeder lines 1575 connecting hub 1561 to base segments 1521 to deliver coolant to solid lithium layer 1536 as structure 1511 is rotated about axis Y by motor assembly 1550. The hub and associated lines or channels are more clearly seen in FIG. 15D, which is a back view of rotatable structure 1511. Also, segment 1522 is shown in FIG. 15C and FIG. 15D in cutaway view showing channels in the segment to deliver coolant behind lithium layer 1536. Rotatable structure 1511 is rotated about axis Y, and proton beam 1590 strikes solid lithium layer 1536 as it rotates past, thereby generating neutrons, which exit through the back of the target. Thus, for this disk-shaped rotatable structure, the proton beam is directed along a path that is substantially parallel to the axis of rotation.

These examples also have the benefit of minimizing the amount of lithium needed as the neutron source target. Since coolant is circulated through lines or channels extending from the central hub to the base segments, heat is thereby removed from the solid target as it rotates, minimizing overheating and blistering and allowing thinner solid targets to be used compared to methods using a stationary target. The heat generated is spread over a large area as the target rotates, while also maintaining the neutron source in a small region, as is desirable for most applications. In addition, the rotatable disk-shaped structure can be positioned vertically, horizontally, or at any angle desired, depending on the position of the target of the generated neutron beam. This provides the present system with considerable design flexibility. Furthermore, the base segments may be individually removable from the rotatable structure for fast, robotic removal of the neutron source material for replacement or system maintenance. For example, a segmented solid lithium target could be used on separate yet attached base segments, as shown in FIG. 15C and FIG. 15D. Detachment of the segments from, for example, the portion of the base comprising coolant and feeder channels allows for quick and easy removal and replacement, minimizing downtime for maintenance or neutron source replacement and would also significantly reduce the radiation hazard to maintenance personnel. Additional benefits are also possible, given the benefit of the present disclosure.

The neutrons produced by the systems and methods of the present disclosure can be used in a variety of different applications. For example, the resulting neutrons can be used for isotope production, explosive and/or fissile materials detection, for assaying of precious metal ores, or in various imaging and medical techniques. As a specific example, the neutrons can be included as part of a boron neutron capture therapy (BNCT) for treatment of cancer.

Figure 16:
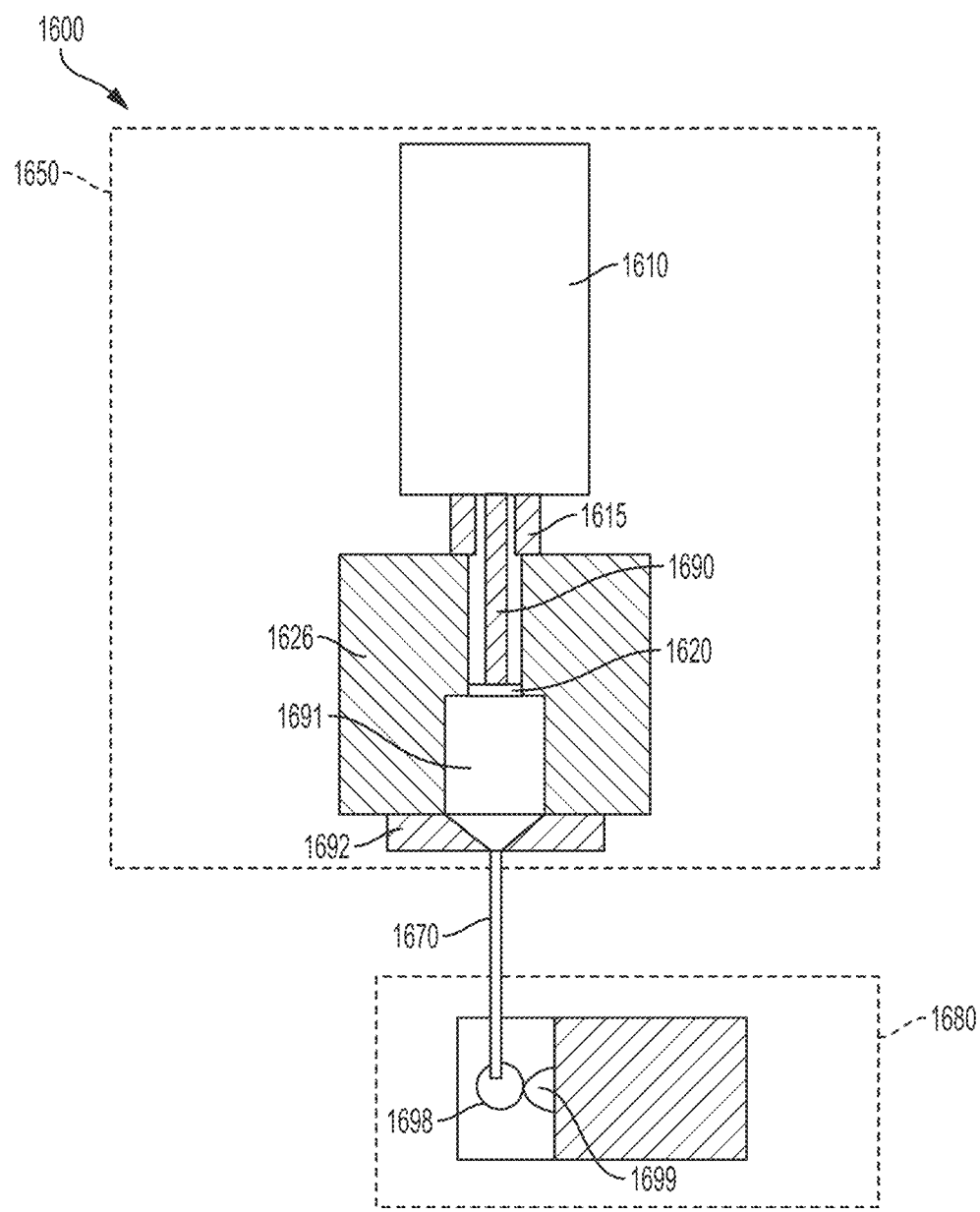
FIG. 16 is a schematic drawing, on cross-section, of a BNCT system in accordance with some embodiments of the present disclosure.

A general schematic of an embodiment of the present BNCT system and method is shown in FIG. 16, as well as, in part, in FIG. 15A. For example, referring to FIG. 16, which is not drawn to scale, BNCT system 1600 includes neutron generating system 1650 and patient positioning and treatment system 1680. Neutron generating system 1650 includes proton beam generator 1610 and neutron source target 1620, which is provided on a rotatable structure (not shown). Any of the rotatable structures of the present disclosure and described above can be used. Proton beam generator 1610 can be provided in a variety of different positions relative to neutron source target 1620, depending upon, for example, the size and design of the facility in which they are placed. Various known bending or focusing magnets can be used to direct the generated proton beam to the target.

Proton beam 1690, produced by proton beam generator 1610, passes through beam transport system 1615, which may include, for example, various types of focusing magnets, and reacts with neutron source target 1620, thereby generating neutrons, which are generally produced in multiple directions around the source depending on their energy—higher energy neutrons moving forward from the target and lower energy neutrons scattering perpendicular to or back from the source. To generate neutron beam 1670 having the desired energy and direction for BNCT treatment, neutron generating system 1650 further includes reflector 1626, beam moderator 1691, and beam collimator 1692. Any neutron beam reflector, moderator, or beam collimator/delimiter known in the art can be used, and each can be positioned around the target as desired in order to capture neutrons having the desired energy range. For example, reflector 1626 can be positioned around the sides and behind the target, as shown in FIG. 16 (As well as in FIG. 15A, at 1526), and can comprise any material known in the art that is relatively non-absorbent to neutrons, such as high atomic number material (including lead, bismuth, or alumina), or carbonaceous materials (including graphite). In this way, low energy back-scattered neutrons are reflected back into the system, thereby protecting or shielding surrounding components as well as patient 1699. The forward-directed, relatively higher energy neutrons can be captured by moderator 1691 (also comprising materials that are relatively non-absorbent to neutrons), in order to reduce their energy to a desired epithermal range. In this way, for example, neutrons having an initial energy of approximately 500 keV can be reduced to a final energy of from about 1 eV to about 10 keV, which is a range desirable for BNCT treatment. Suitable moderator materials are known in the art and include, for example, $D_2O$, MgF, LiF, $AlF_3$, Al, Teflon, and mixtures thereof. Finally, as shown, beam collimator 1692 can be positioned after moderator 1691 to produce and focus the desired neutron beam onto target 1698 in patient 1699.

As shown in FIG. 16, BNCT system 1600 further includes patient positioning and treatment system 1680 which includes equipment and controls for delivering the neutron beam to the patient. For example, a boron delivery system and protocol are used in which the chosen boron-containing treating agent is delivered to patient 1699 at the prescribed dose in order to produce target 1698. Control systems are used to accurately position the target to coincide with expected neutron beam path, and such control systems would be known to one skilled in the art. Additional equipment and components can also be used as needed and would also be well known in the field.

As used herein, the terms "about" and "approximately" generally mean plus or minus 10% of the value stated, e.g., a value of about 250 would include 225 to 275, and about 1,000 would include 900 to 1,100.

The foregoing description of preferred embodiments of the present disclosure has been presented for the purposes of illustration and description. It is not intended to be exhaustive or to limit the invention to the precise forms disclosed. Modifications and variations are possible in light of the above teachings, or may be acquired from practice of the invention. The embodiments presented herein were chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A method, comprising:
   rotating a plurality of wedge-shaped neutron-producing segments forming a circular surface removably coupled to a rotary fixture at a frequency between 100 RPM and 1800 RPM, each of the neutron-producing segments of the plurality of neutron-producing segments including a solid neutron source layer and a substrate, the substrate comprising a coolant channel circuit comprising a plurality of radially-oriented linear channels and a periphery region at an outer circumferential edge of the substrate defined therein, the coolant channel circuit in fluid communication with a coolant inlet and a coolant outlet, wherein the coolant channel circuit is arranged to facilitate coolant to flow from the coolant inlet radially outward through the channels into the periphery region and from the periphery region radially inward through the channels to the coolant outlet;
   flowing a coolant through the coolant channel circuits of the plurality of segments; and
   directing a proton beam at the solid neutron source material such that the proton beam contacts a surface of each of a sequence of segments of the plurality of segments sequentially as the rotary fixture rotates, to cause the emission of neutrons from the solid neutron source layer.

2. The method of claim 1, wherein the proton beam has an energy of between 1.88 MeV and 3 MeV.

3. The method of claim 1, wherein the proton beam has a current of between 10 mA and 100 mA.

4. The method of claim 1, wherein the proton beam contacts the surfaces of each of the sequence of segments of the plurality of segments with a beam spot size of 10 cm.

5. The method of claim 1, wherein the frequency is 1,000 RPM.

6. The method of claim 1, wherein the channels are micro-channels having a cross-sectional dimension of between 0.5 mm and 3 mm.

7. The method of claim 1, wherein the channels are oriented parallel to a major surface of the solid neutron source layer.

8. The method of claim 1, wherein a thickness of the solid neutron source layer is between 0.01 mm and 3 mm.

9. The method of claim 1, wherein the emitted neutrons have an energy between 1 eV and 10 keV.

10. The method of claim 1, wherein the emitted neutrons have a flux of $1\times10^9$ n/cm$^2$/s.

* * * * *